United States Patent [19]

Ingendoh et al.

[11] Patent Number: 4,678,797
[45] Date of Patent: Jul. 7, 1987

[54] BIOLOGICALLY ACTIVE AGENTS CONTAINING SUBSTITUTED ISOXAZOLIDINES

[75] Inventors: Axel Ingendoh, Velbert; Friedrich Berschauer, Wuppertal; Benedikt Becker, Mettmann; Wilhelm Stendel, Wuppertal; Bernhard Homeyer, Leverkusen; Martin Scheer; Anno de Jong, both of Wuppertal; Gerd Hänssler; Paul Reinecke, both of Leverkusen, all of Fed. Rep. of Germany

[73] Assignee: Bayer Aktiengesellschaft, Leverkusen, Fed. Rep. of Germany

[21] Appl. No.: 733,449

[22] Filed: May 10, 1985

[30] Foreign Application Priority Data

May 17, 1984 [DE] Fed. Rep. of Germany ....... 3418395

[51] Int. Cl.$^4$ ............................................. A61K 31/42
[52] U.S. Cl. .................... 514/378; 514/340; 514/380; 514/326; 514/333; 514/316; 514/230; 514/238
[58] Field of Search ................ 548/240; 514/378, 340, 514/380, 326, 333, 316, 230, 238; 544/137, 367; 546/208

[56] References Cited

U.S. PATENT DOCUMENTS 4,197,408 4/1980 Aratani et al. ...................... 560/124

FOREIGN PATENT DOCUMENTS

| 2317980 | 10/1973 | Fed. Rep. of Germany . |
| 2365391 | 9/1974 | Fed. Rep. of Germany . |
| 2362780 | 6/1975 | Fed. Rep. of Germany . |
| 14215 | 6/1968 | Japan . |
| 18294 | 6/1970 | Japan . |
| 167277 | 12/1980 | Japan . |
| 344073 | 3/1960 | Switzerland . |

OTHER PUBLICATIONS

Juranic et al. CA 90:151267b.
Dalgari et al. CA 102:24529e.
Mzengeza et al. CA 101:191748m.
Vasella et al. CA 87:118030j.
Fornefeld et al. J. Org. Chem., vol. 44, No. 5, 1979, pp. 835–839.
Omodei-Sale CA 133415n, vol. 80.
Chemical Abstracts, vol. 79, No. 5, 8/6/73, p. 382, Abstract 31132e.
Beilsteins Handbuch der Organischen Chemie, Springer, Berlin 1928, p. 188, "O-sek.-Butyl-Hydroxylamin . . . ".
Reagents for Organic Synthesis, vol. 6, 1977, p. 538.

Primary Examiner—Jane T. Fan
Attorney, Agent, or Firm—Sprung Horn Kramer & Woods

[57] ABSTRACT

Substituted isoxazolidines of the formula

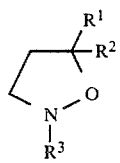

in which
R$^1$ represents optionally substituted alkyl, cycloalkyl, aralkyl, aryl or heteroaryl or radicals of the formula —COR$^4$,
R$^4$ represents optionally substituted alkyl, aryl, alkoxy, alkylthio, aroxy, arylthio, amino, alkylamino, dialkylamino, arylamino, arylalkylamino, diarylamino or cycloalkylamino, or optionally substituted heterocyclic radicals which are bonded via nitrogen,
R$^2$ represents hydrogen or the radicals mentioned for R$^1$, it being possible for R$^1$ and R$^2$ to be identical or different, and
R$^3$ represents optionally substituted alkyl, cycloalkyl, alkenyl, alkinyl or aryl, or saturated heterocyclic radicals, which are optionally substituted, and acid salts thereof, are pesticidally active and increase animals' utilization of feed. Intermediates therefor are also new.

8 Claims, No Drawings

BIOLOGICALLY ACTIVE AGENTS CONTAINING SUBSTITUTED ISOXAZOLIDINES

The present invention relates to biologically active agents containing substituted isoxazolidines as active compounds, and to new isoxazolidines and processes for their preparation.

Substituted isoxazolidines have already been disclosed. However, nothing is known of their biological properties, and, in particular, the suitability of these isoxazolidines as agents for combating pests and agents for increasing the feed utilization in animals. (J. Org. Chem 44, 45 (1979) pages 835–839).

It has been found that substituted isoxazolidines of the formula

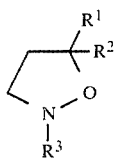

in which $R^1$ represents optionally substituted alkyl, cycloalkyl, aralkyl, aryl or heteroaryl or radicals of the formula —$COR^4$,
wherein
  $R^4$ represents optionally substituted alkyl, aryl, alkoxy, alkylthio, aroxy, arylthio, amino, alkylamino, dialkylamino, arylamino, arylalkylamino, diarylamino or cycloalkylamino, or optionally substituted heterocyclic radicals which are bonded via nitrogen,
$R^2$ represents hydrogen or the radicals mentioned for $R^1$, it being possible for $R^1$ and $R^2$ to be identical or different, and
$R^3$ represents optionally substituted alkyl, cycloalkyl, alkenyl, alkinyl, aryl or aralkyl, or saturated or unsaturated heterocyclic radicals, which are optionally substituted,
and their enantiomers and diastereomers and salts with inorganic and organic acids are suitable as biologically active agents. Biologically active agents are, in particular, agents for combating parts and agents for increasing the feedstuff utilization of animals.

Preferred compounds of the formula I which may be mentioned are those in which $R^1$ represents $C_{1-5}$-alkyl, $C_{3-6}$-cycloalkyl, phenyl-$C_{1-4}$-alkyl, phenyl, naphthyl or pyridyl, which can be mono- or polysubstituted by nitro, OH, CN, halogen, $C_{1-4}$-alkyl, $C_{3-6}$-cycloalkyl, $C_{1-4}$-alkoxy, $C_{1-4}$-alkylthio, $C_{3-2}$-alkylenedioxy, $C_{1-4}$-halogenoalkyl, $C_{1-4}$-alkoxycarbonyl, carboxyl (COOH), amino, $C_{1-4}$-alkylamino, di-$C_{1-4}$-alkylamino, arylamino, aryl-$C_{1-4}$-alkylamino, aminocarbonyl-$C_{1-4}$-alkyl, (—NHCO$C_{1-4}$-alkyl), $C_{1-4}$-alkylsulphonylamino (—NHSO$_2C_{1-4}$-alkyl), $C_{1-4}$-halogenoalkoxy, $C_{1-4}$-halogenoalkylthio, $C_{1-4}$-alkylenedioxy, $C_{1-4}$-halogenoalkylenedioxy, aryl, such as phenyl, or aryloxy, such as phenoxy, or represents a radical of the formula —$COR^4$,
wherein
  $R^4$ represents $C_{1-4}$-alkyl, phenyl, $C_{1-4}$-alkoxy, $C_{1-4}$-alkylthio, phenoxy, phenylthio, amino, $C_{1-4}$-alkylamino, di-$C_{1-4}$-alkylamino, phenylamino, naphthylamino, phenyl-$C_{1-4}$-alkylamino, diphenylamino, $C_{3-6}$-cycloalkylamino, morpholino, piperidino, pyridino, imidazolino, piperazino or triazolino. it being possible for these radicals to be substituted by one or more of the substituents listed above,
$R^2$ represents hydrogen or one of the radicals mentioned under $R^1$, it being possible for $R^1$ and $R^2$ to be identical or different, and
$R^3$ represents $C_{1-10}$-alkyl, $C_{3-8}$-cycloalkyl, $C_{2-4}$-alkenyl, $C_{2-4}$-alkinyl, phenyl, naphthyl or adamantyl, or represents $C_{1-6}$-alkyl, which is substituted by halogen, OH, CN, amino, $C_{1-4}$-alkylamino, $C_{1-4}$-dialkylamino, $C_{1-4}$-alkoxy, $C_{3-6}$-cycloalkyl, optionally substituted phenyl, naphthyl, phenoxy, phenylthio or oxycarbonyl-$C_{1-4}$-alkyl (OCO—$C_{1-4}$-alkyl), or represents phenyl which is substituted by halogen, NO$_2$, CN, OH, amino, $C_{1-4}$-alkylamino, di-$C_{1-4}$-alkylamino or carbonyl-($C_{1-4}$-alkoxy), (—COO—$C_{1-4}$-alkyl), or represents optionally substituted phenoxy, naphthyloxy or biphenyloxy.

Other compounds of the formula I which may be mentioned as particularly preferred are those in which $R^1$ represents optionally substituted phenyl, pyridyl, $C_{1-5}$-alkyl or naphthyl, or represents a radical of the formula —$COR^4$,
wherein
  $R^4$ represents $C_{1-4}$-alkoxy, in particular methoxy or ethoxy, or, furthermore,
  $R^1$ represents phenyl which is one or polysubstituted by identical or different substituents. Substituents which may be mentioned are halogen, such as fluorine, chlorine bromine, $C_{1-4}$-alkyl, in particular methyl or propyl, methoxy, ethoxy, nitro, trifluoromethyl, trifluoromethoxy, CN, —COOH$_3$, COOH, amino, —NHCOCH$_3$, methylenedioxy and optionally halogen-substituted phenoxy,
  $R^1$ furthermore represents $C_{1-5}$-alkyl, which is mono- or polysubstituted by halogen, cyclopropyl, cyclohexyl, hydroxyl, $C_{1-4}$-alkoxy, in particular methoxy, or phenyl which is optionally substituted by halogen or methoxy,
  $R^1$ furthermore represents pyridyl, which is substituted by methyl or halogen, in particular chlorine.
$R^2$ represents hydrogen, phenyl, $C_{1-4}$-alkyl, in particular methyl or propyl, chlorophenyl or a radical of the formula —$COR^4$,
wherein
  $R^4$ represents $C_{1-4}$-alkoxy, in particular methoxy or ethoxy, or di-$C_{1-4}$-alkylamino, in particular diethylamino.
$R^3$ represents $C_{1-6}$-alkyl, in particular methyl, ethyl, propyl, t-butyl, i-pentyl or pinacolyl, optionally substituted by cyclopropyl, halogen, in particular fluorine, OH or phenyl, which is optionally substituted by fluorine or trifluoromethyl, or represents optionally substituted naphthyl, adamantyl, phenoxy, halogenophenoxy, naphthyloxy or biphenyloxy.

Compounds of the formula I in which the radicals have the following meanings may be mentioned specifically:

| $R^1$ | $R^2$ | $R^3$ |
|---|---|---|
| CH$_3$ | CO$_2$CH$_3$ | Cl–⌬–CH$_2$— |

-continued

| R¹ | R² | R³ |
|---|---|---|
| 4-Cl-3-Cl-C₆H₃ | H | —C(CH₃)₂—CHO with extra CH₃ |
| CONH₂ | H | —C(CH₃)₂—CH₂—(2-CF₃-C₆H₄) |
| CO₂C₂H₅ | H | —C(CH₃)₂—CH₂—(2-CF₃-C₆H₄) |
| 4-Cl-C₆H₄ | H | —C(CH₃)₂—CH₂—CH₃ |
| 3-PhO-C₆H₄ | H | —C(CH₃)₂—CH₂—CH₃ |
| 3-PhO-C₆H₄ | H | cyclohexyl |
| 3-(4-Cl-C₆H₄-O)-C₆H₄ | H | cyclohexyl |
| HO—CH₂— | H | —C(CH₃)₃ |
| 3-PhO-C₆H₄ | H | 1-(n-C₄H₉)-1-(CH₃)-cyclobutyl-CH₃ |
| 4-Cl-C₆H₄ | H | 1-CH₃-1-(3,5-Cl₂-C₆H₃)-cyclobutyl-CH₃ |
| 3-PhO-C₆H₄ | H | 1-CH₃-1-(3,5-Cl₂-C₆H₃)-cyclobutyl-CH₃ |
| C₆H₁₁ (cyclohexyl) | —C₂H₅ | —(CH₂)₅—CH₃ |
| Ph | | —(CH₂)₂—C(CH₃)₃ |
| CO₂C₂H₅ | n-C₄H₉ | —(CH₂)₂—C₆H₁₁ |

-continued

| R¹ | R² | R³ |
|---|---|---|
| CONH₂ | n-C₃H₇ | —CH₂—C(CH₃)(OH)—CH₂—C(CH₃)₂—CH₃ |
| C₆H₅ | cyclobutyl | —CH₂—(dicyclopentyl) |
| 2-methylpyrazinyl | n-C₄H₉ | —CH₂—C(CH₃)(dicyclopropyl) |

The formation of diastereomers and enantiomers may be illustrated by the following example:

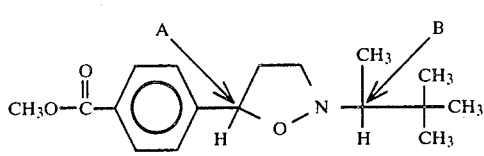

The carbon atoms A and B are chiral. According to the Cahn-Ingold-Prelog nomenclature, the following configurations are possible:

1. A(R)+B(R)
2. A(S)+B(R)
3. A(R)+B(S)
4. A(S)+B(S)

Combinations 1. and 4. are enantiomers. Combinations 2. and 3. are enantiomers. Combinations 1. and 3. are diastereomers. Combinations 3. and 4. are diastereomers.

The following acids which can form salts with the isoxazolidines of the formula I may be mentioned as preferred: HCl, H₂SO₄, HSO₄⁻, H₃PO₄, HPO₄⁻, HClO₄, HBr, HI HF, HNO₃, H₂CO₃, HCO₃⁻, H₃BO₃, HN₃, acetic acid, oxalic acid, malonic acid, succinic acid, malic acid, tartaric acid, maleic acid, fumaric acid, methanesulphonic acid, benzoic acid, substituted benzoic acids, formic acid, chloroacetic acid, toluenesulphonic acid, benzenesulphonic acid, trichloroacetic acid, fluoroacetic acid, phthalic acid, naphthalenesulphonic acid, nicotinic acid, citric acid and ascorbic acid.

Compounds of the formula I which may be mentioned as preferred for agents for combating pests are those in which R³ represents optionally substituted branched alkyl; possible substituents are halogen, in particular chlorine or fluorine, cyclopropyl, cyclohexyl, hydroxyl, C₁₋₄-alkoxy, in particular methoxy, or phenyl which is optionally monosubstituted or polysubstituted by halogen, C₁₋₄-halogenoalkyl, in particular CF₃, or methoxy; and R¹ and R² have the meanings and preferred meanings mentioned above. These agents for combating pests are particularly preferably suitable as insecticides and acaricides.

Compounds of the formula I which may be mentioned as preferred for feedstuff additives are those in which $R^1$ represents optionally substituted aryl, the radicals mentioned in the preferred definitions also being particularly preferred here.

$R^2$ represents hydrogen and $R^3$ has the abovementioned meanings and preferred meanings.

The new compounds of the formula I

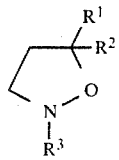   I in which $R^1$ and $R^2$ have the abovementioned meaning and the abovementioned preferred meanings and $R^2$ represents alkyl with more than 3 C atoms or substituted alkyl, or furthermore represents optionally substituted cycloalkyl, alkenyl, alkinyl or aryl, or represents saturated or unsaturated heterocyclic radicals, which are optionally substituted, and their enantiomers and diastereomers have also been found.

The new compounds of the formula I which may be mentioned as preferred are those in which the radicals $R^1$ and $R^2$ have the abovementioned preferred meanings and $R^3$ represents $C_{3-10}$-alkyl, or represents $C_{1-6}$-alkyl, which is substituted by halogen, OH, CN, amino, $C_{1-4}$-alkylamino, di-$C_{1-4}$-alkylamino, $C_{1-4}$-alkoxy, $C_{3-6}$-cycloalkyl, optionally substituted phenyl, naphthyl, phenoxy, phenylthio or oxycarbonyl-$C_{1-4}$-alkyl, or represents phenyl, which is optionally substituted by halogen, $NO_2$, CN, OH, amino, $C_{1-4}$-alkylamino, di-$C_{1-4}$-alkylamino or carbonyl-$C_{1-4}$-alkoxy.

New compounds of the formula I which may be mentioned as particularly preferred are those, in which the radicals $R^1$ and $R^2$ have the radicals mentioned above as particularly preferred and $R^3$ represents i-propyl, t-butyl, i-pentyl or pinacolyl, or represents methyl, ethyl, i-propyl, t-butyl, i-pentyl or pinacolyl, substituted by cyclopropyl, halogen, in particular fluorine, OH or phenyl, which is optionally substituted by fluorine or trifluoromethyl, or represents naphthyl.

The new compounds of the formula I

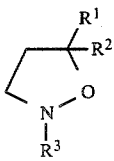

in which $R^1$ and $R^2$ have the abovementioned meaning or the abovementioned preferred meanings and $R^3$ represents alkyl with more than 3 C atoms or substituted alkyl, or represents optionally substituted cycloalkyl, alkenyl, alkinyl or aryl, or represents saturated or unsaturated heterocyclic radicals, which are optionally substituted, are obtained by a process in which hydroxylamines of the formula II

   II in which $R^3$ has the abovementioned meaning, are reacted with formaldehyde and alkenes of the formula III

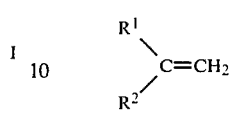   III in which $R^1$ and $R^2$ have the abovementioned meaning.

Some of the hydroxylamines of the formula II are new. The new hydroxylamines of the formula V

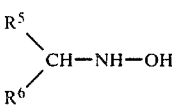   V in which $R^5$ represents branched alkyl, cycloalkyl, alkenyl or alkinyl, which are optionally substituted by halogen, aryloxy, alkoxy, halogenoalkyl or halogenoalkoxy, or furthermore represents aryl or aralkyl, substituted by halogen, alkoxy, alkyl, halogenoalkyl or halogenoalkoxy, and $R^6$, independently of $R^5$, has the meanings given for $R^5$, and salts with inorganic and organic acids of these compounds, have been found.

Hydroxylamines of the formula V are obtained by a process in which (a) oximes of the formula VI

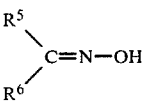   VI in which the radicals $R^5$ and $R^6$ have the abovementioned meaning, are reduced, for example with $NaBH_3CN$ or diborane, in a weakly acid alcoholic solution, or (b) nitro compounds of the formula

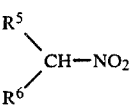

are reduced, for example with hydrogen (catalyst) or zinc dust.

Oximes of the formula VI are known or they can be prepared analogously to known processes.

Some of the alkenes of the formula III are new. The new alkenes of the formula VII

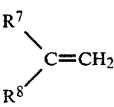   VII in which $R^7$ represents hydrogen and $R^8$ represents radicals of the formulae

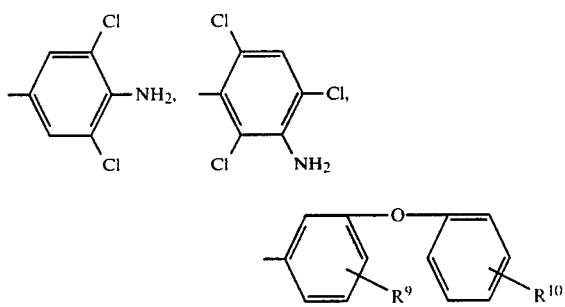

wherein $R^9$ and $R^{10}$ independently of one another represent hydrogen, halogen (in particular fluorine) or trifluoromethyl, but $R^9$ and $R^{10}$ should not simultaneously represent hydrogen, have been found.

Alkenes of the formula VII are obtained by a process in which (a) halogenoalkyls of the formula VIII $$R^8-CH_2-Hal \qquad VIII$$

in which $R^8$ has the abovementioned meaning, are reacted with triphenylphosphine and the product is then reacted with formaldehyde in the presence of a base, or (b) an aldehyde of the formula IX $$R^8-CHO \qquad IX$$

in which $R^8$ has the abovementioned meaning, is olefinized in a Wittig reaction in a manner which is known per se.

The process for the preparation of the new compounds of the formula I can be carried out by bringing together and reacting the hydroxylamines of the formula II, formaldehyde and the alkenes of the formula III. It can be represented by the following equation:

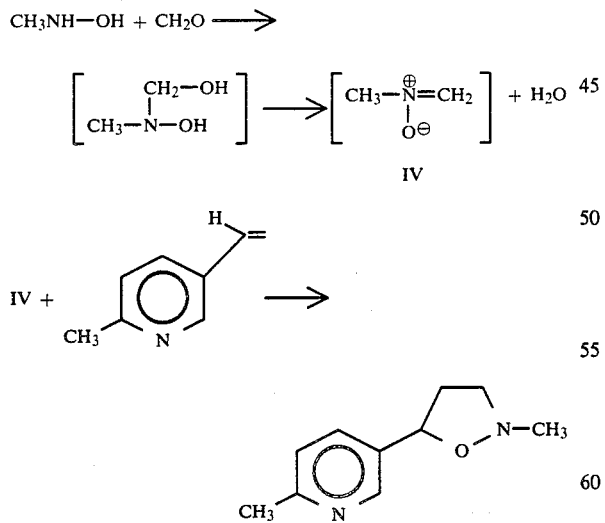

The following known hydroxylamines of the formula II may be mentioned as particularly preferred:

$CH_3NHOH$, NHOH, Phenyl-$CH_2$—NHOH,

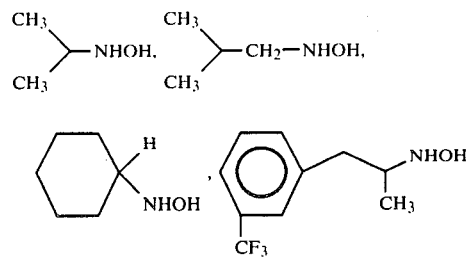

and 1-adamantylhydroxylamine.

The following new hydroxylamines of the formula V may be mentioned as particularly preferred:

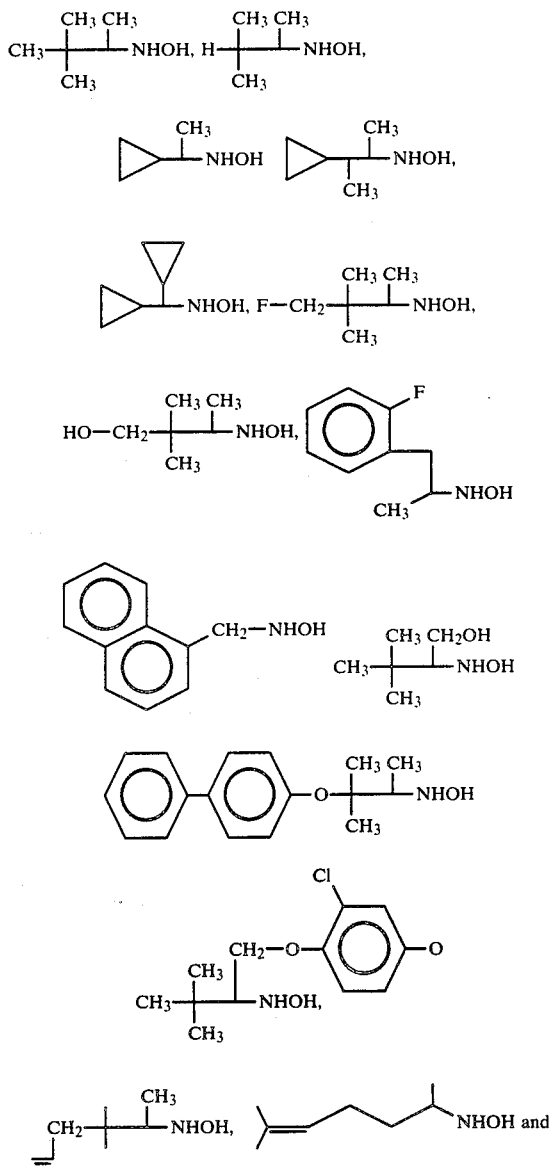

The reaction is carried out at temperatures of 0°–100° C., preferably at 100°–140° C. The starting compounds of the formulae II and III and formaldehyde are brought together in approximately equimolar amounts. The formaldehyde can also be employed in excess (about a 1-5-fold excess).

The reaction is usually carried out under normal pressure. However, it is also possible to carry out the reaction under pressure. It is preferably carried out in the presence of diluents. Suitable diluents are hydrocarbons, such as toluene, xylene or benzene, halogenohydrocarbons, such as chloroform, alcohols, such as ethanol or isopropanol, and ethers, such as tert.-butyl methyl ether.

It is also possible to add formaldehyde to the hydroxylamines of the formula II and then to add the alkenes of the formula III to the reaction mixture.

In a particularly preferred procedure, it is also possible to react the hydroxylamines of the formula II in the form of their salts with inorganic or organic acids, in particular HCl, and formaldehyde, preferably as paraformaldehyde in the form of its aqueous formalin solution (3–40%) or with trioxane, and then to add the alkene of the formula III to the reaction solution.

For this, formaldehyde, such as, for example, formalin, is added to the salts of the hydroxylamines of the formula II in suitable diluents and the mixture is then neutralized with strong inorganic or organic bases.

The reaction is carried out at temperatures from −20° to +150° C. under normal pressure.

The starting compounds are brought together in an approximately equimolar ratio. Formaldehyde can also be employed in excess (in about a 1-5-fold excess).

Suitable diluents which may be mentioned are inert organic diluents, such as alcohols, such as methanol, ethanol or isopropanol, hydrocarbons, such as toluene, dimethylformamide, dimethyl sulphoxide, high-boiling ethers, chlorohydrocarbons, such as chloroform, methylene chloride or ethylene chloride.

As strong inorganic bases his alkali and alkaline earth metal hydroxides, such as sodium hydroxide solution or potassium hydroxide solution, alkali and alkaline earth metal carbonates and bicarbonates.

Suitable organic bases which may be mentioned are: Trimethylamine, triethylamine, N-ethyldiisopropylamine, N,N-dimethylaniline, N,N-diethylaniline, N,N,N',N'-tetramethylethylenediamine, N,N,N',N'-tetraethylethylenediamine, lutidine, picoline and pyridine.

The neutralization is carried out at about −20° to +160° C. to a pH value of 6–8.

The alkene of the formula III and a "water-entraining agent" are then added to the reaction mixture.

The reaction mixture is then heated to 110° to 140° C., depending on the boiling point of the water-entraining agent. The alcohol and water are distilled off azeotropically with the aid of the water-entraining agent.

Water-entraining agents which may be mentioned are: Aromatic hydrocarbons, such as, in particular, benzene, toluene or xylene, and halogenated hydrocarbons, such as chloroform or carbon tetrachloride.

After the alcohol has been distilled off and the water has been removed from the reaction mixture with the water-entraining agent, the mixture is allowed to after-react at 110°–140° C. and is then worked up in the customary manner.

As already mentioned, the hydroxylamines of the formula V are new. The process for their preparation can be characterized by the following equation:

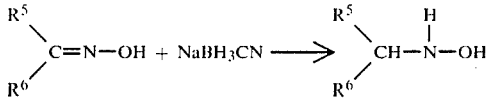

The reaction is carried out at −20° to +100° C., preferably at 20° C.

The reaction is carried out under normal pressure.

The starting components are employed in approximately an equimolar ratio.

The reaction is carried out in diluents. Diluents which may be mentioned are: alcohols, such as methanol, ethanol, isopropanol and ethylene glycol. The reaction can also be carried out in aqueous alcohols.

The pH value of the reaction solution is about 1–4. The pH value can be determined by means of a calibrated glass electrode. It is furthermore suitable to add a color indicator, such as bromocresol green or methyl orange, for adjustment of the pH value.

Working up can be effected in a manner which is known per se by acidification of the batch with concentrated acid, such as hydrochloric acid, in order to destroy the cyanoborohydride, and subsequent alkalization, followed by extraction of the N-alylhydroxylamine with organic solvents (compare R. Borch J. Am. Chem. Soc. 93, 2897 (1971).

However, it is particularly advantageous, when the borohydride reduction has ended and the borohydride has been destroyed with concentrated acids, such as hydrochloric acid, to concentrate the batch under a water pump vacuum, and to extract the residue with chloroform, methylene chloride or alcohols, such as ethanol, isopropanol or methanol. The organic solution of the N-alkylhydroxylamine hydrochloride is dried with sodium sulphate or other suitable drying agents and concentrated in a rotary evaporator.

The compounds of the formula V can also be prepared in a manner which is known per se by reduction of the corresponding nitro compounds with hydrogen under catalysis by, for example, palladium-on-charcoal (compare U.S. Pat. No. 3,173,953), or by reduction with zinc dust in glacial acetic acid, with aluminum amalgam or with tin-II chloride (compare Houben-Weyl Methoden der org. Chemie [Methods of organic chemistry] Volume 10/1 page 1153).

As already mentioned, the alkenes of the formula VII are new. The process for their preparation can be characterized by the following equation:

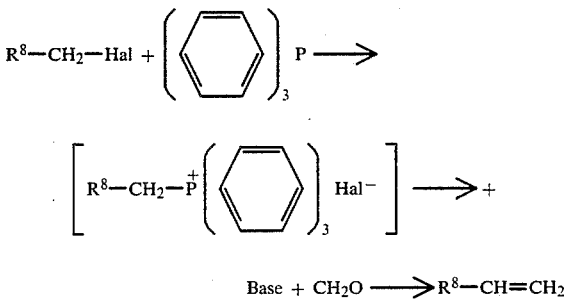

Halogenomethyl compounds of the formula VIII which may be mentioned are: 2-CN-, 2-CH$_3$-, 3-NO$_2$-, 3-NO$_2$-5-methoxy-, 3-NO$_2$-5-ethoxy or 2,4-dimethylbenzyl chloride and naphthylmethyl chloride.

The reaction is carried out at −20° to +100° C., preferably at 20° C.

The reaction is carried out under normal pressure.

The starting compounds are employed in approximately equivalent proportions, a 1-10-fold excess of formalin being used.

The reaction is carried out in the presence of diluents. Diluents which may be mentioned for the olefination are water and alcohols (methanol, ethanol or isopropanol).

Another process for the preparation of the alkenes of the formula VII can be characterized by the following equation:

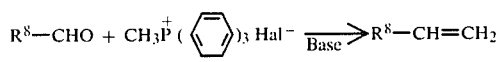

Aldehydes of the formula IX which may be mentioned are: 2-Chloro-3,4-methylenedioxy-, 2,4,6-trichloro-5-amino-3,5-dibromo-4-methoxy-, 3-nitro-4-chloro-, 3-phenoxy-3-(4-chlorophenoxy)- and 3-(3-trifluoromethylphenoxy)-benzaldehyde and 3-pyridylaldehyde.

The process is carried out analogously to the process described by R. Broos et al., Synthetic Comm 6(1) 53-57 (1976) and W. S. Emmerson Chem Rev. Volume 45 (1949) page 347.

The reaction is carried out under the usual conditions for a Wittig olefinization. The aldehydes of the formula IX employed are known.

Suitable olefinizing agents according to Wittig are phosphorus ylides, such as $Ph_3P^{\oplus}\text{-}CH_3Cl^{\ominus}$ or $Br^{\ominus}$ or $I^{\ominus}$.

The reaction is carried out at 20°-120° C., preferably at 80° C. It is carried out under atmospheric pressure.

The reaction is carried out in diluents. Diluents which may be mentioned are: Alcohols, such as methanol or ethanol, hydrocarbons, such as benzene or toluene, ethers, such as diethyl ether, dioxane or tetrahydrofuran, and halogenohydrocarbons, such as methylene chloride.

The bases used are: Amides, such as lithium diisopropylamide or $NaNH_2$, hydrides, such as NaH, alkali metal carbonates and alkaline earth metal carbonates, such as $K_2CO_3$, alkali metal hydroxides and alkaline earth metal hydroxides, such as KOH or NaOH, and alkali metal alcoholates and alkaline earth metal alcoholates, such as Na tert.-butanolate.

The active compounds are well tolerated by plants, have a favorable level of toxicity of warm-blooded animals, and are suitable for combating animal pests, especially insects, arachnids and nematodes, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and *Scutigera* spec. From the order of the Symphyla, for example *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta american, Leucophaea maderae, Blattella germanica, Acheta domesticus,* Gryllotalpa spp., *Locusta migratoria migratorioides, Melanoplus differentialis* and *Schistocerca gregaria.* From the order of the Dermaptera, for example, *Forficula auricularia.* From the order of the Isoptera, for example, Reticulitermes spp. From the order of the Anoplura, for example, *Phylloxera vastatrix,* Pemphigus spp., *Pediculus humanus corporis,* Haematopinus spp. and Linognatus spp. From the order of the Mallophaga, for example, Trichlodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Phodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Pysylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichloplusia ni, Carpocapsa pomonella,* Pieris spp., Chilo spp., *Pyrausta nubilalis, Ephestia kuehni\*lla, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Brucchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.* From the order of the Siphonaptera, for example, *Xenopyslla cheopis* and Ceratophyllus spp. From the order of the Arachnida, for example, *Scorpio maurus* and *Latrodectus mactans.*

The active compounds according to the invention exhibit a powerful microbicidal action and can be employed in practice for combating undesired microorganisms. The active compounds are suitable for use as plant protection agents.

Fungicidal agents in plant protection are used for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonadaceae, Rhizobiaceae, Enterobacteriaceae, Corynebacteriaceae and Streptomycetaceae.

The good toleration, by plants, of the active compounds in the concentrations required for combating plant diseases permit treatment of above-ground parts of plants, of vegetative propagation stock and seeds, and of the soil.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is emulsifiers and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellant gas, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohols ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as naturally occurring phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussion Blue, and organic dyestuffs, such as alizarin dyestuffs, azo dyestuffs and metal phthalocyanine dyestuffs, and trace nutrients such as salts of iron, manganese, boron, copper, cobalt molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms and the like.

The active compounds according to the invention can furthermore be present in their commercially available formulations and in the use forms, prepared from these formulations, as a mixture with synergistic agents. Synergistic agents are compounds which increase the action of the active compounds, without it being necessary for the added synergistic agent to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as good stability to alkali on limed substrates.

The active compounds according to the invention are also suitable for combating ectoparasites and endoparasites in the field of verterinary medicine.

The active compounds according to the invention are used in a known manner in the veterinary sector, such as by oral administration, for example in the form of tablets, capsules, drinks and granules, by dermal application, for example in the form of dipping, spraying, pouring on and spotting on, and dusting, and by parenteral administration, for example in the form of an injection.

The active compounds can be used in all areas of animal husbandry as agents for promoting and accelerating growth and for improving the feedstuff utilization of healthy and sick animals.

The activity of the active compounds is largely independent of the species and sex of the animals. The active compounds have proved particularly useful in the rearing and keeping of young animals and fattening animals.

The following stock animals and pets may be mentioned as examples of animals for which the active compounds can be used for promoting and accelerating growth, for improving the feedstuff utilization and for improving the flesh/fat ratio in the carcass: Warm-blooded animals, such as cattle, pigs, horses, sheep, goats, cats, dogs, rabbits, fur-bearing animals, for example mink and chinchilla, poultry, for example chickens, geese, ducks and turkeys, pigeons, parrots and canaries, and cold-blooded animals, such as fish, for example carp, and reptiles, for example snakes.

The amounts of active compounds administered to the animals to achieve the desired effect can be varied substantially because of the advantageous properties of the active compounds. It is preferably about 0.01 to 50, in particular 0.1 to 10 mg/kg of body weight per day. The period of administration can be from a few hours or days up to several years. The appropriate amount of active compound and the appropriate period of administration depend, in particular, on the species, age, sex, state of health and nature of housing and feeding of the animals, and can easily be determined by any expert.

The active compounds are administered to the animals by the usual methods. The nature of the administration depends, in particular, on the species, the behavior and the state of health of the animals. Thus, administration can be effected orally or parenterally, once or several times daily at regular or irregular intervals.

For reasons of expediency, oral administration, in particular in the rhythm of the intake of food and/or drink by the animals, is in most cases to be preferred.

The active compounds can be administered as a pure substance mixture or in formulated form, that is to say mixed with any desired type of non-toxic inert carriers, for example with carriers and in formulations such as are usual in nutritional preparations.

The active compounds, optionally in formulated form, are administered in a suitable form together with pharmaceutically active compounds, mineral salts, trace elements, vitamins, proteins, fats, colorants and/or flavoring agents.

Oral administration together with the feed and/or drinking water is recommended, the active compound being added to the total amount or only to portions of the feed and/or drinking water, as required.

The active compounds can be admixed to the feed and/or drinking water in accordance with customary methods by simple mixing as a pure substance mixture, preferably in finely divided form, or in formulated form as a mixture with edible non-toxic carriers, if appropriate in the form of a premix or a feed concentrate.

The feed and/or drinking water can contain, for example, the active compounds in a weight concentration of about 0.01 to 50 ppm, in particular 0.1 to 10 ppm. The optimum level of the concentration of the active compounds in the feed and/or drinking water depends, in particular, on the amount of feed and/or drinking water taken in by the animals, and can easily be determined by an expert.

The nature of the feed and its composition is irrelevant here. All the customary or specific feed compositions, which preferably contain the usual equilibrium of energy substances and builder substances, including vitamins and minerals, necessary for balanced nutrition, can be used. The feed can be composed, for example, of vegetable substances, for example hay, beet, cereals and cereal by-products, animal substances, for example meat, fats and bonemeal, fish products, vitamins, for example vitamin A, D complex and B complex, proteins, aminoacids, for example DL-methionine, and inorganic substances, for example lime and sodium chloride.

Feed concentrates contain the active compounds, alongside edible substances, for example rye flour, corn flour, soy bean flour or lime, if appropriate with further nutrients and builder substances, as well as proteins, mineral salts and vitamins. They can be prepared by the customary methods of mixing.

Preferably, in premixes and feed concentrates, the active compounds can, if appropriate, also be protected from air, light and/or moisture by suitable agents which coat their surface, for example with non-toxic waxes or gelatin.

The following is an example of the composition of a feed for rearing chicks, which contains an active compound according to the invention: 200 g of wheat, 340 g of corn 361 g of coarse soy bean meal, 60 g of beef tallow, 15 g of dicalcium phosphate, 10 g of calcium carbonate, 4 g of iodized sodium chloride, 7.5 g of a vitamin/mineral mixture and 2.5 g of an active compound premix give, after thorough mixing, 1 kg of feed.

One kg of feed mix contains: 600 international units of Vitamin A, 100 international units of Vitamin $D_3$, 10 mg of Vitamin E, 1 mg of Vitamin $K_3$, 3 mg of riboflavin, 2 mg of pyridoxine, 20 mcg of Vitamin $B_{12}$, 5 mg of calcium pantothenate, 30 mg of nicotinic acid, 200 mg of choline chloride, 200 mg of $MnSO_4 \times H_2O$, 140 mg of $ZnSO_4 \times 7H_2O$, 100 mg of $FeSO_4 \times 7H_2O$ and 20 mg of $CuSO_4 \times 5H_2O$.

The active compound premix contains the active compounds in the desired amount, for example 10 mg, and in addition 1 g of DL-methionine as well as soy bean flour in an amount such that 2.5 g of premix are formed.

The following is an example of the composition of a feed for rearing pigs, which contains an active compound according to the invention: 630 g of shredded cereal feed (composed of 200 g of corn 150 g of shredded barley, 150 g of shredded oats and 130 g of shredded wheat), 80 g of fish meal, 60 g of coarse soy bean meal, 60 g of tapioca meal, 38 g of brewer's yeast, 50 g of a vitamin/mineral mixture for pigs (composition, for example, as for the thick feed), 30 g of linseed cake meal, 30 g of corn gluten feed, 10 g of soy bean oil, 10 g of sugar cane molasses and 2 g of an active compound premix (composition, for example, as for the chick feed) give, after thorough mixing, 1 kg of feed.

The feed mixtures described are intended preferably for rearing and fattening chicks or pigs, but they can also be used, in the same or a similar composition, for rearing and fattening other animals.

Several feeding experiments have been carried out with the active compounds according to the invention. The following results were obtained:

EXAMPLE 1a

| (a) Animal characteristics and feed | |
|---|---|
| (a 1) Rats, female | |
| (a 2) Number | 30 |
| (a 3) Strain | SPF Wistar, Breeder: Hagemann |
| (a 4) Weight | 90–150 g |
| (a 5) Condition | good |
| (a 6) Feed | |
| Raw nutrients* | |
| Raw protein | 19.0 |
| Raw fat | 4.0 |
| Raw fiber | 6.0 |
| Ash | 7.0 |

| | |
|---|---|
| Water | 13.5 |
| N-free extractive | 50.5 |
| Metabolizable energy: | |
| Kcal/kg | 3100 |
| KJ/kg | 13000 |
| Minerals* | |
| Calcium | 0.9 |
| Phosphorus | 0.7 |
| Magnesium | 0.2 |
| Sodium | 0.2 |
| Vitamins** | |
| Standard diet | |
| Vitamin A | 15,000 international units |
| Vitamin D₃ | 600 international units |
| Vitamin E | 75 mg |
| Vitamin K₃ | 3 mg |
| Vitamin B₁ | 18 mg |
| Vitamin B₂ | 12 mg |
| Vitamin B₆ | 9 mg |
| Vitamin B₁₂ | 24 mcg |
| Nicotinic acid | 36 mg |
| Pantothenic acid | 21 mg |
| Folic acid | 2 mg |
| Biotin | 60 mg |
| Choline | 600 mg |
| Vitamin C | 36 mg |
| Aminoacids* | |
| Lysine | 0.9 |
| Methionine + cystine | 0.6 |
| Phenylalanine + tyrosine | 1.4 |
| Arginine | 1.1 |
| Histidine | 0.4 |
| Tryptophan | 0.2 |
| Threonine | 0.6 |
| Isoleucine | 0.9 |
| Leucine | 1.3 |
| Valine | 0.9 |
| Trace elements** | |
| Manganese | 75.0 |
| Iron | 135.0 |
| Copper | 13.0 |
| Zinc | 70.0 |
| Iodine | 0.9 |
| Fluorine | 9.0 |

*% in the diet (mean value)
**mg in 1 kg of diet (mean value)

(b) Treatment of the animals

The animals were acclimated to the new housing conditions for 2 days, the experimental feed generally being administered without the added active compound. On the third day of the experiment, the animals were randomized and the experimental groups then formed so that both the mean values and the deviations in body weights were identical between the groups. A preliminary period of 5 days was followed by a main period of 8 days, during which the feed intake, additional growth and feed utilization were determined.

The following treatments were tested:

(b 1) Negative control (n = 24)
(b 2) 100 ppm (active compound of Example 49) (n = 6)
(c) Result (feed intake, growth, feed utilization) during the entire experimental period (13 days)

| | Feed intake (g) | Additional growth (g) | Feed utilization (g/g) |
|---|---|---|---|
| (c 1) Negative control | 177.3 | 35.4 | 5.01 |
| (c 2) 100 ppm (active compound of Example 49) | 182.8 | 39.7 | 4.61 |

EXAMPLE 1b (a) Animal characteristics and feed (a 1) Rats, female
(a 2) Number       27
(a 3) Strain         SPF Wistar, Breeder: Hagemann
(a 4) Weight       90–150 g
(a 5) Condition   good
(a 6) Feed
Raw nutrients, minerals, vitamins, formic acid and trace elements, and treatment of the animals
- as in Example 1a -

The following treatments were tested:

(b 1) Negative control (n = 21)
(b 2) 25 ppm (active compound from Example 11) (n = 6)
(c) Result (feed intake, growth, feed utilization) during the entire experimental period (13 days)

| | Food intake (g) | Additional growth (g) | Feed utilization (g/g) |
|---|---|---|---|
| (c 1) Negative control | 181.5 | 33.0 | 5.59 |
| (c 2) 25 ppm (active compound of Example 11) | 183.3 | 36.8 | 4.99 |

EXAMPLE 1c (a) Animal characteristics and feed (a 1) Rats, female
(a 2) Number       30
(a 3) Strain         SPF Wistar, Breeder: Hagemann
(a 4) Weight       90–150 g
(a 5) Condition   good
(a 6) Feed
Raw nutrients, minerals, vitamins, formic acid and trace elements, and treatment of the animals
- as in Example 1a -
The following treatments were tested:
(b 1) Negative control (n = 24)
(b 2) 1 ppm (active compound from Example 6) (n = 6)
(b 3) 25 ppm (active compound from Example 6) (n = 6)
(c) Result (feed intake, growth, feed utilization) during the entire experimental period (13 days)

| | Food intake (g) | Additional growth (g) | Feed utilization (g/g) |
|---|---|---|---|
| (c 1) Negative control | 187.1 | 39.4 | 4.78 |
| (c 2) 1 ppm (acive compound of Example 6) | 189.5 | 42.6 | 4.50 |
| (c 3) 25 ppm (active compound of Example 6) | 193.5 | 46.0 | 4.20 |

EXAMPLE

Pyricularia test (rice)/systemic
Solvent: 12.5 parts by weight of acetone
Emulsifier: 0.3 parts by weight of alkylaryl polyglycol ether To produce a suitable preparation of active compound, 1 part by weight of active compound is mixed with the stated amounts of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of *Pyricularia oryzae*. Thereafter, the plants remain in a greenhouse at a temperature of 25° C.

and a relative atmospheric humidity of 100% until they are evaluated.

Evaluation of the disease infestation is carried out 4 days after the inoculation.

In this test, a clearly superior activity compared with the prior art is shown, for example, by the compounds according to the following preparation examples:

EXAMPLE

Pyricularia test (rice)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amounts of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, a clealy superior activity compared with the prior art is shown, for example, by the compounds according to the following preparation examples:

EXAMPLE

Laphygma test
Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the owlet moth (*Laphygma frugiperda*), as long as the leaves are still moist.

After the specified period of time, the destruction in % is determined. 100% means that all the caterpillars have been killed; 0% means that none of the caterpillars have been killed.

In this test, for example, the following compounds from the preparation examples show a superior activity compared to the prior art:

EXAMPLE

Critical concentration test/soil insects
Test insect: *Phorbia antiqua* grubs (in the soil)
Solvent: 3 parts by weight of acetone
Emulsifier: 1 part by weight alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/liter) being decisive. The soil is filled into pots and the pots are left to stand at room temperature.

After 24 hours, the test insects are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, for example, the following compounds from the preparation examples show a superior action compared to the prior art:

PREPARATION EXAMPLES

General working instructions:

A solution of 0.1 mol of the alkene of the formula III in 250 ml of toluene is heated to 100° C., and an alcoholic aqueous solution obtained by adding 0.11 mol of an aqueous formalin solution (33% strength) to 0.11 mol of hydroxylamine hydrochloride of the formula II, neutralizing with potassium hydroxide solution (1 molar in methanol) and filtering off the potassium chloride, is added.

Methanol initially thereby distils off, and the mixture is then warmed to an external temperature of 140° C. Water thereby distils off azeotropically. The mixture is boiled under reflux for a further 5 hours. It is allowed to cool, solid residues are filtered off and 100 ml of 10% strength hydrochloric acid are added. The mixture is extracted twice with 100 ml of ether and the aqueous residue is rendered alkaline to pH 8-10 with concentrated aqueous sodium hydroxide solution. The mixture is again extracted three times with 100 ml of ether each time. The combined ether extracts are dried over sodium sulphate, the ether is distilled off and the residue is distilled under a high vacuum or reacted with ethanolic hydrochloric acid to give the hydrochloride or reacted with ethanolic oxalic acid to give the oxalate.

The following compounds are obtained by these general instructions.

General formula:

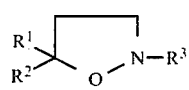

| | $R^1$ | $R^2$ | $R^3$ | Yield | $^1$H—NMR-CDCl$_3$: δ/ppm | physical data |
|---|---|---|---|---|---|---|
| 1 | 2-pyridyl | H | CH$_3$ | 76% | | b.p. 65° C./ 0.1 mbar |
| 2 | phenyl | benzyl | CH$_3$ | 66% | | b.p. 46° C. m.p. 198 [HCl] |
| 3 | phenyl | CH$_3$ | CH$_3$ | 61% | | b.p. 65° C. 0.25 mbar m.p. 120° C. [HCl] |
| 4 | 3-pyridyl | H | CH$_3$ | 68.5% | | b.p. 140° C. 0.22 mbar |
| 5 | phenyl | H | C(CH$_3$)$_3$ | 62.7% | | m.p. 160° C. [HCl] |
| 6 | 2-methyl-5-pyridyl | H | CH$_3$ | 63.8% | | b.p. 90° C. 2 mbar |
| 7 | cyclohexyl-(CH$_2$)$_5$— | CO$_2$C$_2$H$_5$ | CH$_3$ | 45% | | b.p. 138° C. 0.02 mbar |
| 8 | phenyl-(CH$_2$)$_2$— | CO$_2$C$_2$H$_5$ | CH$_3$ | 57% | | b.p. 112–5° C. 0.02 mbar |
| 9 | 2-methyl-5-pyridyl | H | C(CH$_3$)$_3$ | 26% | | b.p. 82–5° C. 0.2 mbar |
| 10 | 3-nitrophenyl | H | CH$_3$ | 66% | | m.p. 148° C. [HCl] |
| 11 | 3,4-dichlorophenyl | H | CH$_3$ | 79% | | b.p. 98% 0.2 mbar m.p. 107° C. [oxalate] |

-continued

General formula:

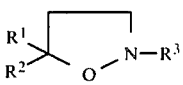

| | R¹ | R² | R³ | Yield | ¹H—NMR-CCD(Cl₃): δ/ppm | physical data |
|---|---|---|---|---|---|---|
| 12 | 3,4-dichlorophenyl | H | C(CH₃)₃ | 65% | | b.p. 115° C. 0.3 mbar m.p. 107° C. [oxalate] |
| 13 | 2-chlorophenyl | H | CH₃ | 55% | | m.p. 93° C. [oxalate] |
| 14 | 2-naphthyl | H | CH₃ | 65% | | m.p. 169° C. [oxalate] |
| 15 | 3-nitrophenyl | H | C(CH₃)₃ | 65% | | m.p. 139° C. [oxalate] |
| 16 | 4-chlorophenyl | H | CH₃ | 79% | | m.p. 130° C. [oxalate] |
| 17 | benzyl (C₆H₅CH₂) | CO₂C₂H₅ | CH₃ | 47% | | m.p. 139° C. [oxalate] |
| 18 | 2,6-dichlorophenyl | H | CH₃ | 54% | | m.p. 156° C. [oxalate] |
| 19 | 3-trifluoromethylphenyl | H | CH₃ | 58% | | m.p. 130° C. [oxalate] |
| 20 | 4-methoxybenzyl (CH₃O-C₆H₄-CH₂—) | CO₂C₂H₅ | CH₃ | 79% | | m.p. 129° C. [oxalate] |

-continued

General formula:

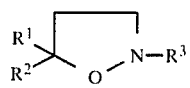

| | R¹ | R² | R³ | Yield | ¹H—NMR-CCD(Cl₃): δ/ppm | physical data |
|---|---|---|---|---|---|---|
| 21 | 2-OCH₃, 5-CH₃O-C₆H₃-CH₂— | CO₂C₂H₅ | CH₃ | 83% | | m.p. 131° C. [oxalate] |
| 22 | 3,4-(CH₃O)₂-C₆H₃-CH₂— | CO₂C₂H₅ | CH₃ | 51% | | m.p. 142° C. [oxalate] |
| 23 | 4-CH₃-C₆H₄— | H | CH₃ | 74% | | m.p. 148° C. [oxalate] |
| 24 | 3-NO₂-C₆H₄— | H | —C(CH₃)₂H with extra CH₃ (tert-butyl-like: C(CH₃)₃ / CH(CH₃)-C(CH₃)₂ ) | 89% | | m.p. 120° C. [oxalate] 142° C. [HCl] |
| 25 | 2,6-Cl₂-C₆H₃— | H | —CH(CH₃)—C(CH₃)₂H type | 58% | | m.p. 139° C. [oxalate] |
| 26 | C₆H₅— | H | —CH₂—phenyl | 55% | | m.p. 124° C. [oxalate] |
| 27 | 3,4-Cl₂-C₆H₃— | CH₃ | —C(CH₃)₃ | 35% | 1.06 [s] | oil |
| 28 | 2-CN-C₆H₄— | H | —CH(CH₃)—C(CH₃)₂H type | 56% | | m.p. 146° C. [oxalate] |
| 29 | 4-CO₂CH₃-C₆H₄— | H | CH₃ | 55% | | m.p. 158° C. [oxalate] |

-continued

General formula:

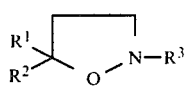

| | $R^1$ | $R^2$ | $R^3$ | Yield | $^1$H—NMR-CCD(Cl$_3$): δ/ppm | physical data |
|---|---|---|---|---|---|---|
| 30 | 4-Cl-C$_6$H$_4$- | CH$_3$ | -C(CH$_3$)$_3$ | 45% | 1.53 [s]<br>1.48 [s]<br>1.2 [s] | oil |
| 31 | 2,4-Cl$_2$-C$_6$H$_3$- | CH$_3$ | -CH(CH$_3$)-C(CH$_3$)$_3$ (as drawn: CH(H)(CH$_3$)C(CH$_3$)$_3$) | 48% | 1.51 [s]<br>1.48 [s]<br>0.96 [s]<br>0.95 [s] | oil |
| 32 | C$_6$H$_5$- | C$_6$H$_5$- | -CH(CH$_3$)-C(CH$_3$)$_3$ | 80% | | m.p. 133° C. [oxalate] |
| 33 | C$_6$H$_5$- | C$_6$H$_5$- | -CH$_2$-phenyl | 67% | | m.p. 143° C. [oxalate] |
| 34 | CH$_3$ | CO$_2$CH$_3$ | -CH$_2$-phenyl | 15% | | m.p. 98° C. [oxalate] |
| 35 | 4-CO$_2$CH$_3$-C$_6$H$_4$- | H | -CH$_2$-phenyl | 29% | | m.p. 99° C. [oxalate] |
| 36 | 4-CO$_2$CH$_3$-C$_6$H$_4$- | H | -CH(CH$_3$)-C(CH$_3$)$_3$ | 81% | | m.p. 162° C. [HCl] |
| 37 | 4-Cl-C$_6$H$_4$- | CH$_3$ | -CH(CH$_3$)-C(CH$_3$)$_3$ | 45% | 1 53 [s]<br>1 46 [s] | 0.97 [s]<br>oil |
| 38 | 2-NHCOCH$_3$-C$_6$H$_4$- | CH$_3$ | -CH(CH$_3$)-C(CH$_3$)$_3$ | 47.3% | | m.p. 118° C. [oxalate] |
| 39 | C$_6$H$_5$-CH$_2$- | CO$_2$C$_2$H$_5$ | -CH(CH$_3$)-C(CH$_3$)$_3$ | 75% | | m.p. 122° C. [oxalate] |

-continued

General formula:

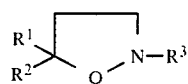

| | R[1] | R[2] | R[3] | Yield | $^1$H—NMR-CCD(Cl$_3$): δ/ppm | physical data |
|---|---|---|---|---|---|---|
| 40 | 2-aminophenyl (with CH$_3$ on ring, NH$_2$) | CH$_3$ | —C(H)(CH$_3$)—C(CH$_3$)$_3$ (CH$_3$ CH$_3$ / H-C-C-CH$_3$ / CH$_3$) | 60% | 0.91 [s] 0.95 [s] 1.63 [s] | oil |
| 41 | benzyl (—CH$_2$—C$_6$H$_5$) | CO$_2$C$_2$H$_5$ | —CH$_2$—phenyl | 68% | | m.p. 117° C. [oxalate] |
| 42 | phenyl | H | —CH$_2$—Ph | 67% | | m.p. 122° C. [oxalate] |
| 43 | 4-Cl-phenyl | H | —C(H)(CH$_3$)—C(CH$_3$)$_3$ | 40% | | m.p. 98° C. [HCl] |
| 44 | 3-CF$_3$-phenyl | H | —C(H)(CH$_3$)—C(CH$_3$)$_3$ | 61% | | m.p. 156° C. [HCl] |
| 45 | benzyl (—CH$_2$—C$_6$H$_5$) | —CO$_2$C$_2$H$_5$ | —C(CH$_3$)$_3$ | 65% | 1.10 [s] 3.08 [bs] | oil |
| 46 | CH$_3$ | —CO$_2$CH$_3$ | —C(H)(CH$_3$)—CH$_2$—(3-CF$_3$-phenyl) | 71% | 0.81 [α × α] 1.29 [s] 1.30 [s] 3.78 [s] | oil |
| 47 | 4-CH$_3$O-benzyl | —CON(C$_2$H$_5$)$_2$ | CH$_3$ | 43% | | m.p. 95–100° C. [oxalate] |
| 48 | 2,4-dichlorophenyl | H | —C(H)(CH$_3$)—C(CH$_3$)$_3$ | 83% | | m.p. 158° C. [HCl] |
| 49 | 2,6-dichlorophenyl | H | —C(CH$_3$)$_3$ | 42% | | m.p. 135° C. [oxalate] |

-continued

General formula:

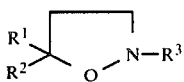

| | R¹ | R² | R³ | Yield | ¹H—NMR-CCD(Cl₃): δ/ppm | physical data |
|---|---|---|---|---|---|---|
| 50 | 2,4-dichlorophenyl | H | CH₃ | 95% | | m.p. 132° C. [oxalate] |
| 51 | 4-chlorophenyl | H | C(CH₃)₃ | 67% | | m.p. 100° C. [oxalate] |
| 52 | 4-chlorophenyl | H | CH(CH₃)₂ | 20% | | m.p. 130° C. [oxalate] |
| 53 | 3-trifluoromethylphenyl | H | C(CH₃)₃ | 68,8% | 1.23 [s] 5.03 [t] | oil |
| 54 | 4-chlorobenzyl | CO₂C₂H₅ | CH₃ | 66% | | m.p. 152° C. [oxalate] |
| 55 | benzyl | CON(C₂H₅)₂ | CH₃ | 43% | 2.60 [s] 2.90 [α × α] | oil |
| 56 | 2,6-dichlorophenyl | H | CH(CH₃)₂ | 45% | | m.p. 169° C. [HCl] |
| 57 | 2,4-dichlorophenyl | CO₂C₂H₅ | CH(CH₃)₂ | 38% | | m.p. 122° C. [oxalate] |
| 58 | 4-chlorobenzyl | CO₂C₂H₅ | CH(CH₃)₂ | 58% | 3.01 [bs] | oil |
| 59 | 3,4-dichlorobenzyl | CO₂C₂H₅ | CH(CH₃)₂ | 52% | 3.03 [bs] | oil |

-continued

General formula:

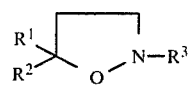

| | R¹ | R² | R³ | Yield | ¹H—NMR-CCD(Cl₃): δ/ppm | physical data |
|---|---|---|---|---|---|---|
| 60 | 4-Cl-C₆H₄-CH₂- | CO₂C₂H₅ | -C(CH₃)₃ | 33% | 1.11 [s]<br>3.06 [bs] | oil |
| 61 | 3,4-Cl₂-C₆H₃-CH₂- | CO₂C₂H₅ | -C(CH₃)₃ | 55% | 1.08 [s]<br>3.05 [bs] | oil |
| 62 | 3-CF₃-C₆H₄- | H | -CH(CH₃)₂ | 87% | | m.p. 123° C. [oxalate] |
| 63 | 3-NO₂-C₆H₄- | H | -CH(CH₃)₂ | 62% | | m.p. 142° C. [oxalate] |
| 64 | 2-naphthyl | H | -CH(CH₃)₂ | 60% | | m.p. 125° C. [oxalate] |
| 65 | 3-NO₂-C₆H₄- | H | -CH₂-CH(CH₃)₂ | 28.5% | | m.p. 106° C. [oxalate] |
| 66 | 3-NO₂-C₆H₄- | H | -CH(CH₃)-CH(CH₃)₂ | 35% | 5.05 [t] | oil |
| 67 | 3-Cl-C₆H₄- | H | CH₃ | 25% | | m.p. 97° C. [oxalate] |
| 68 | 2,4-Cl₂-C₆H₃- | H | -CH(CH(CH₃)₂)- (with H) | 47.9% | | m.p. 141° C. [oxalate] |

-continued

General formula:

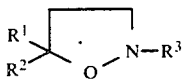

| | R¹ | R² | R³ | Yield | ¹H—NMR-CCD(Cl₃): δ/ppm | physical data |
|---|---|---|---|---|---|---|
| 69 | 2-chlorophenyl | H | C(CH₃)₃ | 67% | | m.p. 159° C. [HCl] |
| 70 | 6-chloro-1,3-benzodioxol-5-yl | H | CH₃ | 50.6% | | m.p. 134° C. [oxalate] |
| 71 | 3-methylphenyl | H | C(CH₃)₃ | 43% | | m.p. 100° C. [oxalate] |
| 72 | 2-cyanophenyl | H | CH(CH₃)₂ | 15% | | m.p. 95° C. [oxalate] |
| 73 | 2-(trifluoromethyl)phenyl | H | CH(CH₃)(C(CH₃)... ) CH(CH₃)C(CH₃)₃ | 68% | | m.p. 160° C. [HCl] |
| 74 | 2,4-dichlorophenyl | H | CH(CH₃)C(CH₃)₃ | 54% | | m.p. 110° C. [HCl] |
| 75 | 4-chlorophenyl | H | —CH₂—CF₃ | 76.5% | | m.p. 123-5° C. [HCl] |
| 76 | 3-nitrophenyl | H | CH(CH₃)(cyclopropyl) | 36% | | m.p. 114° C. [oxalate] |
| 77 | 2,4-dichlorophenyl | H | CH(CH₃)(cyclopropyl) | 42.8% | | m.p. 132° C. [oxalate] |

-continued

General formula:

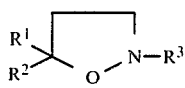

| | R[1] | R[2] | R[3] | Yield | [1]H—NMR-CCD(Cl$_3$): δ/ppm | physical data |
|---|---|---|---|---|---|---|
| 78 | 2,4-dimethylphenyl | H | CH(CH$_3$)-C(CH$_3$)$_2$- (with terminal H) | 39% | | m.p. 176° C. [HCl] |
| 79 | 2-methylphenyl | H | -C(CH$_3$)$_3$ type (tert-butyl variant) | 71.8% | | m.p. 181° C. [HCl] |
| 80 | CH$_3$ | CO$_2$CH$_3$ | -C(CH$_3$)$_3$ | 50% | 0.66 [s]<br>1.35 [s]<br>1.36 [s]<br>3.63 [s] | oil |
| 81 | 2,4-dichlorophenyl | H | dicyclopropylmethyl | 45% | | m.p. 125° C. [oxalate] |
| 82 | 3-nitrophenyl | H | dicyclopropylmethyl | 34% | | m.p. 104° C. [oxalate] |
| 83 | 3,5-dichlorophenyl | CH$_3$ | -C(CH$_3$)$_3$ variant | 32% | | m.p. 131° C. [oxalate] |
| 84 | 2,4-dichlorophenyl | H | -CH(CH$_3$)-C(CH$_3$)$_2$-CH$_2$F | 37% | | m.p. 150° C. [HCl] |
| 85 | 2,4-dichlorophenyl | H | 1-methylcyclopropyl-CH(CH$_3$)- | 13% | 0.33 [mult]<br>5.23 [t] | oil |
| 86 | 3-nitrophenyl | H | 1,1-dimethylcyclopropyl | 33% | | m.p. 150° C. [HCl] |

-continued

General formula:

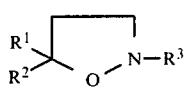

| | R¹ | R² | R³ | Yield | ¹H—NMR-CCD(Cl₃): δ/ppm | physical data |
|---|---|---|---|---|---|---|
| 87 | 3-nitrophenyl | H | -C(CH₃)₂-CH₂-F | 36% | | m.p. 132° C. [oxalate] |
| 88 | 3-phenoxyphenyl | H | -CH(CH₃)-C(CH₃)₂-H (neopentyl-like: H,CH₃/CH₃,CH₃) | 30% | | m.p. 91° C. [HCl] |
| 89 | 3-isopropyl-5-trifluoromethylphenyl | CH₃ | -C(CH₃)₂-C(CH₃)₃ | 55% | 0.96 [s] 1.00 [s] 1.50 [s] 1.56 [s] | oil |
| 90 | 3-methoxy-4-nitrophenyl | H | -C(CH₃)₂-C(CH₃)₃ (tert-pentyl) | 39% | | m.p. 185° C. [HCl] |
| 91 | 4-ethoxy-3-nitrophenyl (C₂H₃O) | H | -C(CH₃)₂-C(CH₃)₃ | 56% | | m.p. 185° C. [HCl] |
| 92 | 2-(NHSO₂CH₃)phenyl | CH₃ | -C(CH₃)₂-C(CH₃)₃ | 42% | | m.p. 205° C. [HCl] |
| 93 | 2,4-dichlorophenyl | H | -CH₂-C(CH₃)₃ | 56% | | m.p. 91° C. [oxalate] |
| 94 | 4-nitrophenyl | H | CH₃ | 88% | | m.p. 175° C. [HCl] |
| 95 | 2,4-dichlorophenyl | H | -CH(CF₃)-CH₃ | 73.9% | | m.p. 123° C. [HCl] |

-continued

General formula:

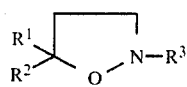

| | R[1] | R[2] | R[3] | Yield | $^1$H—NMR-CCD(Cl$_3$): δ/ppm | physical data |
|---|---|---|---|---|---|---|
| 96 | 1-naphthyl | H | —C(CH$_3$)$_2$CH(CH$_3$)— (CH$_3$ CH$_3$ / CH$_3$) | 25.7% | | m.p. 184° C. [HCl] |
| 97 | 4-Cl-C$_6$H$_4$— | H | —CH(CF$_3$)CH$_3$ | 49% | | m.p. 92° C. [HCl] |
| 98 | 3-NO$_2$-C$_6$H$_4$— | H | —CH$_2$—C(CH$_3$)$_3$ | 51% | | m.p. 133° C. [oxalate] |
| 99 | 4-OCH$_3$-C$_6$H$_4$— | H | CH$_3$ | 81% | | m.p. 142° C. [oxalate] |
| 100 | 4-NO$_2$-C$_6$H$_4$— | H | —C(CH$_3$)$_2$C(CH$_3$)$_3$ | 59% | | m.p. 103° C. [oxalate] |
| 101 | 2,4,6-tri-Cl-3-NH$_2$-C$_6$H— | H | —C(CH$_3$)$_3$ | 73% | 1.18 [s] 5.53 [t] | oil |
| 102 | 2,4,6-tri-Cl-3-NH$_2$-C$_6$H— | H | —C(CH$_3$)$_2$C(CH$_3$)$_3$ | 38% | 0.93 [s] 5.56 [t] | oil |
| 103 | 4-Cl-C$_6$H$_4$— | H | —CH$_2$—C(CH$_3$)$_3$ | 35% | | m.p. 99° C. [oxalate] |
| 104 | 2-naphthyl | H | CH$_3$ | 31% | | m.p. 165° C. [HCl] |

-continued

General formula:

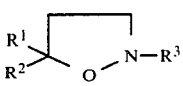

| | R¹ | R² | R³ | Yield | ¹H—NMR-CCD(Cl₃): δ/ppm | physical data |
|---|---|---|---|---|---|---|
| 105 | 2,6-dibromo-4-methoxyphenyl (OCH₃, Br, Br) | H | —C(CH₃)₃ | 45.8% | | m.p. 188° C. [HCl] |
| 106 | 4-NO₂-phenyl | H | —C(CH₃)₃ | 76% | | m.p. 113° C. [oxalate] |
| 107 | 3,4-dimethoxyphenyl (OCH₃, OCH₃) | H | —CH(CH₃)₂ | 36.6% | | m.p. 135° C. [oxalate] |
| 108 | 3-Cl-4-NO₂-phenyl | H | —CH(CH₃)₂ | 60.7% | | m.p. 109° C. [oxalate] |
| 109 | 3-Cl-4-NO₂-phenyl | H | —CH₂—CF₃ | 85% | 5.13 [t] | oil |
| 110 | 3-Cl-4-NO₂-phenyl | H | —C(CH₃)₃ | 71% | | m.p. 117° C. [oxalate] |
| 111 | 3,4-dichlorophenyl | —CH(CH₃)₂ | —C(CH₃)₂CH₂CH₃ (actually C(CH₃)₂... see image) | 25% | 0.80 [s] | oil |
| 112 | 4-OCF₃-phenyl | H | —C(CH₃)₂—C(CH₃)... | 67.8% | 0.81 [s] 4.13 [t] | oil |
| 113 | 3-NO₂-phenyl | H | —CH(CH₃)CH₂-(2-F-phenyl) | 45% | 1.16 [d] 5.11 [t] | oil |

-continued

General formula:

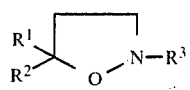

| | $R^1$ | $R^2$ | $R^3$ | Yield | $^1$H—NMR-CCD(Cl$_3$): δ/ppm | physical data |
|---|---|---|---|---|---|---|
| 114 | 4-Cl-C$_6$H$_4$— | —CH(CH$_3$)$_2$ | —C(CH$_3$)$_2$CH(CH$_3$)$_2$ (neopentyl-type: C(CH$_3$)$_2$—CH$_3$ with extra CH$_3$) | 25% | 1.16 [s] | oil |
| 115 | CH$_3$ | —CO$_2$CH$_3$ | —CH$_2$-(1-naphthyl) | 61% | 1.16 [s]<br>1.18 [s]<br>3.73 [bs]<br>4.43 [a × a] | oil |
| 116 | 4-Cl-C$_6$H$_4$— | 4-Cl-C$_6$H$_4$— | —C(CH$_3$)$_3$ (t-butyl with extra CH$_3$) | 77% | 1.01 [bs] | oil |
| 117 | 4-Cl-C$_6$H$_4$— | 4-Cl-C$_6$H$_4$— | —CH(CH$_3$)$_2$ | 77% | | m.p. 162° C. [oxalate] |
| 118 | 2-CF$_3$-C$_6$H$_4$— | H | —CH(CH$_3$)—CH$_2$-(3-CF$_3$-C$_6$H$_4$) | 91% | | m.p. 127° C. [HCl] |
| 119 | (CH$_3$)$_2$C(OCH$_3$)—CH(CH$_3$)— | H | —C(CH$_3$)$_3$ | 42% | 3.26 [s]<br>1.43 [s]<br>1.30 [s]<br>1.00 [s]<br>0.88 [s] | oil |
| 120 | (cyclopropyl)$_2$C(OH)— | H | —C(CH$_3$)$_3$ | 52% | 0.40 [bs]<br>0.93 [s] | oil |
| 121 | 4-Cl-C$_6$H$_4$—C(CH$_3$)(OH)— | H | —C(CH$_3$)$_3$ | 58.3% | 1.00 [s]<br>1.60 [s]<br>1.58 [s] | oil |
| 122 | (4-Cl-C$_6$H$_4$)(C$_6$H$_5$)C(OH)— | H | —C(CH$_3$)$_3$ | 34% | 5.06 [2 × t]<br>0.83 [bs] | oil |

-continued

General formula:

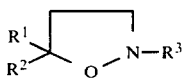

| | $R^1$ | $R^2$ | $R^3$ | Yield | $^1$H—NMR-CCD(Cl$_3$): δ/ppm | physical data |
|---|---|---|---|---|---|---|
| 123 | 4-Cl-C$_6$H$_4$-C(OH)(CH$_3$)-C$_6$H$_4$-4-Cl | H | CH(CH$_3$)-C(CH$_3$)$_3$ | 40% | 4.96 [2 × t] 0.76 [s] | oil |
| 124 | C$_6$H$_5$— | H | CH(CH$_3$)-C$_6$H$_4$-2-F (via CH$_2$) | 42% | 5.06 [2 × t] 1.06 [bd] | oil |
| 125 | 2,3-Cl$_2$-C$_6$H$_3$-CH$_2$— | CO$_2$C$_2$H$_5$ | CH$_3$ | 93% | | 137° C. [oxalate] |
| 126 | 1-naphthyl-O-CH$_2$— | H | C(CH$_3$)$_3$ | 60% | 2.05–2.50 [mult] 1.10 [s] | |
| 127 | (CH$_3$SO$_2$)$_2$N-(2-Cl-4-Me-C$_6$H$_3$)— | H | C(CH$_3$)$_3$ | 30% | | 1.59–61° C. |
| 128 | 2,4-Cl$_2$-C$_6$H$_3$— | H | CH(CH$_2$OH)-C(CH$_3$)$_3$ | 38% | 6.00 [t] 1.16 [s] | |
| 129 | 2,4-Cl$_2$-C$_6$H$_3$— | H | CH(CH$_3$)-C(CH$_3$)$_2$-CH$_2$-OC(O)CH$_3$ | 50% | 2.01 [s] 1.01 [s] 0.98 [s] | |
| 130 | 2,6-Cl$_2$-4-NH$_2$-C$_6$H$_2$— | H | C(CH$_3$)$_3$ | 41% | | 217° C. [HCl] |
| 131 | 2,6-Cl$_2$-4-NH$_2$-C$_6$H$_2$— | H | —CH$_2$—C(CH$_3$)$_3$ | 59% | | 162° C. [HCl] |

-continued

General formula:

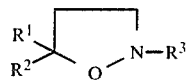

| | R¹ | R² | R³ | Yield | ¹H—NMR-CCD(Cl₃): δ/ppm | physical data |
|---|---|---|---|---|---|---|
| 132 | 4-amino-3,5-dichlorophenyl (NH₂ on ring with 2 Cl) | H | —CH₃ | 73% | 4.98 [t]<br>2.80 [s] | |
| 133 | 2,6-dichloro-4-aminophenyl | H | —C(CH₃)₂—CH(CH₃)— (t-configuration) | 51% | | 177° C. [HCl] |
| 134 | 2,6-dichloro-4-aminophenyl | H | —CH(CH₃)₂ | 60% | | 190° C. [HCl] |
| 135 | naphthyl | H | —C(CH₃)₂—O—C₆H₄—C₆H₅ | 35% | 5.75 [t]<br>1.45 [s]<br>1.35 [s] | |
| 136 | 4-chlorophenyl | H | cyclohexyl | 85% | 5.05 [t] | |
| 137 | naphthyl | H | —C(CH₃)₂—CH₂—O—(2,4-dichlorophenyl) | | 5.68 [t]<br>1.16 [s] | |
| 138 | 1-(naphthyloxymethyl) | H | —C(CH₃)₂—C(CH₃)₃ | 25% | 0.98 [s] | |
| 139 | 4-chloro-2-phenoxyphenyl | H | —C(CH₃)₂—CH₂—O—(2,4-dichlorophenyl) | 10% | | 153° C. [oxalate] |

-continued

General formula:

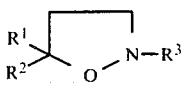

| | R¹ | R² | R³ | Yield | ¹H—NMR-CCD(Cl₃): δ/ppm | physical data |
|---|---|---|---|---|---|---|
| 140 | 3-chloro-phenoxyphenyl | H | -C(CH₃)₂-O-biphenyl | 28% | 4.96 [t] | |
| 141 | phenoxyphenyl | H | -C(CH₃)₂-O-biphenyl | 15% | 5.00 [t] | |
| 142 | 4-chlorophenyl | H | -C(CH₃)₂-O-biphenyl | 31% | 5.02 [t] | |
| 143 | (4-chlorophenoxy)phenyl | H | -C(CH₃)₂-CH₃ (tert-butyl type) | 35% | | 155° C. [HCl] |
| 144 | phenoxyphenyl | H | -C(CH₃)₂-CH₂-O-(2,4-dichlorophenyl) with extra CH₃ | 21% | 5.01 [t] 1.00 [s] | |
| 145 | CH₃— | CO₂CH₃ | -C(CH₃)₂-CH₂-O-(2,4-dichlorophenyl) with extra CH₃ | 61% | 3.76 [s] 3.64 [s] 1.56 [s] 1.40 [s] | |
| 146 | naphthyl | H | -C(CH₃)₂-CH₃ | 65% | 5.60 [t] 1.23 [s] | |
| 147 | phenoxyphenyl | H | -C(CH₃)(cyclopropyl-CH₃) | 23% | 4.83 [t] 1.30 [s] 1.13 [s] 1.00 [s] | |
| 148 | 4-chlorophenyl | H | -C(CH₃)₂-CH₂-O-(2,4-dichlorophenyl) with extra CH₃ | 93% | | 172° C. [HCl] |

-continued

General formula:

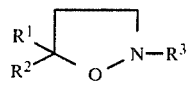

| | R¹ | R² | R³ | Yield | ¹H—NMR-CCD(Cl₃): δ/ppm | physical data |
|---|---|---|---|---|---|---|
| 149 | 3-[N(SO₂CH₃)₂]-phenyl | H | C(CH₃)₃ | 25% | | 146° C. |
| 150 | 2-(3-trifluoromethylphenoxy)phenyl | H | C(CH₃)₃ | 50.5% | 4.83 [ ]<br>0.8 [s] | |
| 151 | 2-(3-trifluoromethylphenoxy)phenyl | H | —C(CH₃)₂—CH₂—O—(2,4-dichlorophenyl) | 78% | 5.20 [t]<br>1.20 [s] | |
| 152 | 4-biphenylyl | H | C(CH₃)₃ | 61% | | 42° C. |
| 153(a) | 4-biphenylyl | H | —C(CH₃)₂—CH₂—O—(2,4-dichlorophenyl) | 53% | 5.05 [t]<br>1.08 [s] | |
| 153(b) | 9-anthryl | H | C(CH₃)₃ | 56% | 6.0–6.5 [m]<br>1.00 [s] | |
| 154 | 3-pyridyl | H | CH₃ | 18% | | 95° C. (oxalate) |
| 155 | 3-pyridyl | H | C(CH₃)₃ | 39% | | 135° C. (oxalate) |
| 156 | 3-pyridyl | H | C(CH₃)₃ | 43% | | 149° C. (oxalate) |

-continued

General formula:

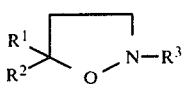

| | R¹ | R² | R³ | Yield | ¹H—NMR-CCD(Cl₃): δ/ppm | physical data |
|---|---|---|---|---|---|---|
| 157 | phenoxyphenyl (O-linked diphenyl ether) | H | 4-methyl-1-(propan-2-ylidene)cyclohexyl | 27% | 5.01 [t] 0.60–1.00 [m] | |
| 158 | phenoxyphenyl | H | 2,6-dimethyl-hept-5-enyl ($CH_3$, $CH_3$, $CH_3$) | 20.5% | 4.90 [t] 1.0–1.5 [m] | |
| 159 | 3-pyridyl | H | $CH(CH_3)_2$ | 32% | 5.00 [t] 1.17 [α] | |
| 160 | phenoxyphenyl | H | $C(CH_3)_2CH_2OH$ (with extra $CH_3$) | 15% | 4.85 [m] | |
| 161 | 2-methylpyridin-5-yl | H | $CH(CH_3)_2$ | 65% | | b.p. 90–93° C. 0.1 mbar |
| 162 | 2-methyl-5-pyridyl | H | $-CH_2-C(CH_3)_3$ | 26% | | b.p. 95–103° C 0.2 mbar |
| 163 | phenoxyphenyl | H | $-C(CH_3)_2-CH(CH_3)-CH=CH_2$ | 25 | 4.95 [t] 0.80–1.1 [m] | |
| 164 | 4-chlorophenyl | H | $-C(CH_3)_2-CH_2OH$ | 41% | 4.93 (t) 3.80 (bs) | oil |
| 165 | 2-methyl-5-pyridyl | H | cyclohexyl | 50.3% | 5.00 (t) 2.53 (bs) | oil |
| 166 | 4-chlorophenyl | $CH_3$ | naphthalen-1-ylmethyl ($CH_2$) | 48% | 4.46 (bs) 1.56 (s) | oil |

-continued

General formula:

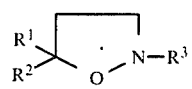

| | R¹ | R² | R³ | Yield | ¹H-NMR-CCD(Cl₃): δ/ppm | physical data |
|---|---|---|---|---|---|---|
| 167 | CH₃O-C(=O)- | H | CH₃-CH(-)-CH₂-C₆H₄-Cl (p) | 40% | 4.53 (bt)<br>3.76 (s) | oil |
| 168 | C₂H₅O-C(=O)- | H | CH₃-CH(-)-CH₂-C₆H₄-CF₃ (m) | 56% | 4.26 (2 × q)<br>1.3 (t)<br>1.0 (d) | oil |
| 169 | H₂N-C(=O)- | H | CH₃-CH(-)-CH₂-C₆H₄-CF₃ (m) | 45% | 4.46 (2 × t)<br>1.30 (m) | oil |
| 170 | CH₃O-C(=O)- | CH₃ | -CH₂-C₆H₄-Cl (o) | 35% | 4.13 (s)<br>3.43 (s)<br>1.53 (s) | oil |
| 171 | 3-(PhO)-C₆H₄- | H | cyclohexyl | 67% | 4.93 (t) | oil |
| 172 | 3-(4-Cl-C₆H₄-O)-C₆H₄- | H | cyclohexyl | 36% | 4.96 (t) | oil |
| 173 | 3-(4-Cl-C₆H₄-O)-C₆H₄- | H | -C(CH₃)₂-CH₂-CH₃ | 45% | 4.86 (t)<br>1.06 (s) | oil |
| 174 | 4-Cl-C₆H₄- | H | -C(CH₃)₂-CH₂-CH₃ | 63% | 4.90 (t)<br>1.06 (s) | oil |
| 175 | 4-Cl-C₆H₄- | H | cyclopropyl-(4-Cl-C₆H₄)-CH(-) | 37% | 4.96 (t) | oil |
| 176 | 4-tBu-C₆H₄- | H | (CH₃)₂CH-CH₂-CH₂-C(CH₃)=CH- | 25% | 4.96 (t)<br>1.30 (s)<br>1.20 (s) | oil |

-continued

General formula:

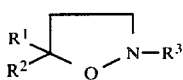

| | R¹ | R² | R³ | Yield | ¹H—NMR-CCD(Cl₃): δ/ppm | physical data |
|---|---|---|---|---|---|---|
| 177 | 4-(t-Bu)-C₆H₄- | H | -C(CH₃)₂-C(CH₃)₃ | 54% | 4.90 (t) 1.33 (s) 0.93 (s) | oil |
| 178 | 2,6-Cl₂-4-(H₂N)-C₆H₂- | H | -CH₂-CH₂-CH₂-CH₃ | 35% | 4.86 (t) 0.91 (bt) | oil |
| 179 | 4-NO₂-C₆H₄- | H | -C(CH₃)₂-CH₂OH | 38% | 85° C. | |
| 180 | (C₆H₅)₂O- (diphenyl ether) | H | -CH(cyclopropyl)-C₆H₄-4-Cl | 25% | 4.96 (t) 0.33 (m) | oil |
| 181 | HO-CH₂- | H | -C(CH₃)₂-CH₂-O-C₆H₃-2,4-Cl₂ | 83% | 1.03 (s) | oil |
| 182 | 3-NO₂-C₆H₄- | H | -CH(CH₃)-CH₂-C₆H₄-4-Cl | 65% | 5.01 (t) 1.01 (bd) | oil |
| 183 | CH₃O-C(=O)- | H | -CH(CH₃)-CH₂-C₆H₄-2-F | 65% | 4.43 (t) 3.68 (s) | oil |
| 184 | 3-NO₂-C₆H₄- | H | -CH(CH₃)-CH₂-C₆H₃-2,3-(OCH₃)₂ | 63% | 5.03 (t) 3.80 (s) 1.03 (bd) | oil |
| 185 | CH₃O-C(=O)- | CH₃ | -CH(CH₃)-CH₂-C₆H₄-4-Cl | 80% | 3.66 (s) 1.46 (s) | oil |
| 186 | 3-NO₂-C₆H₄- | H | -CH(CH₃)-CH₂-C₆H₄-2-OCH₃ | 67% | 5.00 (t) 3.73 (s) | oil |

-continued

General formula:

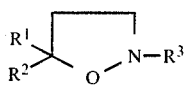

| | R¹ | R² | R³ | Yield | ¹H—NMR-CCD(Cl₃): δ/ppm | physical data |
|---|---|---|---|---|---|---|
| 187 | 3-nitrophenyl | H | CH(CH₃)-CH₂-CH₂-C(CH₃)=CH₂ (as drawn) | 41% | 3.83 (t), 1.13 (s) | oil |
| 188 | 2,4-dichlorophenyl | CONH₂ | CH(CH₃)-CH₂-(3-CF₃-phenyl) | 58% | 5.03 (m), 1.03 (bd) | oil |
| 189 | 4-tert-butylphenyl | H | CH(CH₃)-CH₂-(3-CF₃-phenyl) | 63% | 5.325 (t), 1.33 (s) | oil |
| 190 | CH₃O-C(=O)- | CH₃ | CH(CH₃)-CH₂-(4-F-phenyl) | 67% | 3.78 (s), 1.53 (s), 0.95 (bd) | oil |
| 191 | CH₃O-C(=O)- | H | CH(CH₃)-CH₂-(4-F-phenyl) | 68% | 4.46 (t), 4.37 (s), 2.26 (s) | oil |
| 192 | phenyl | phenyl | CH(CH₃)-CH₂-(4-F-phenyl) | 10% | 7.2 (m), 1.01 (bd) | oil |
| 193 | H₂N-C(=O)- | H | CH(CH₃)-CH₂-(2-F-phenyl) | 75% | 4.45 (2×t), 1.15 (bd), 1.00 (d) | 48° C. |
| 194 | H₂N-C(=O)- | H | CH(CH₃)-CH₂-(4-Cl-phenyl) | 93% | 4.48 (2×t), 1.07 (bd), 1.00 (d) | 83° C. |
| 195 | 2,3-dichlorophenyl | H | CH(CH₃)-CH₂-(2-F-phenyl) | 45% | 5.80 (t), 1.05 (d) | oil |

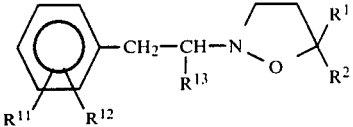
| Nr. | R¹¹ | R¹² | R¹³ | R² | R¹ | 1 H—NMR CDCl/ppm |
|---|---|---|---|---|---|---|
| 196 | 4-Cl | H | CH₃ | 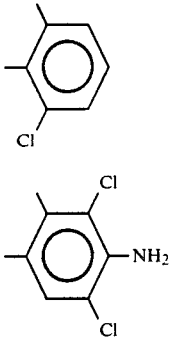 | H | 7,35–7,1 m; 5,76 t; 355–2,8 m, 1,06 d |
| 197 | 4-Cl | H | CH₃ | 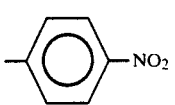 | H | 7,3–7,1 m; 4,8 t; 3,4–2,05 m; 1,03 d |
| 198 | 4-Cl | H | CH₃ | 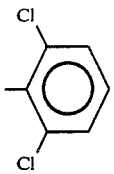 | H | 8,3–7,0 m; 5,06 t; 3,4–2,1 m; 1,03 d |
| 199 | 2-Cl | 6-Cl | CH₃ | 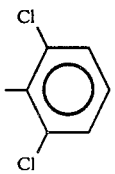 | H | 2,3–2,05 m; 5,75 t; 3,5–2,3 m; 1,1 d |
| 200 | 3-Cl | 4-Cl | CH₃ | 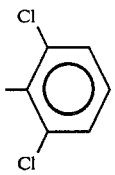 | H | 7,3–7,1 m; 5,75 t; 3,5–2,5 m; 1,03 d |
| 201 | 2-F | 5-Cl | CH₃ | 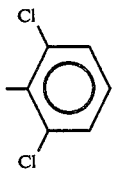 | H | 7,4–7,2 m; 5,75 t; 3,5–2,4 m; 1,88 d |
| 202 | 2-F | 6-Cl | CH₃ | 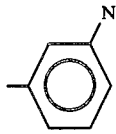 | H | 7,4–7,0 m; 5,83 d × d; 3,5–2,4 m; 1,06 d |
| 203 | 2-F | 6-Cl | CH₃ | 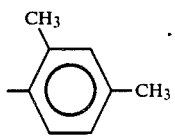 | H | 8,3–7,0 m; 5,16 t; 3,5–2,0 m; 1,10 d |
| 204 | 2-F | H | CH₃ | CH₃ <br> —〈 〉— CH₃ | H | 7,3–7,0 m; 5,2 t; 3,2–2,05 m; 2,3s; 1,12 d |

-continued
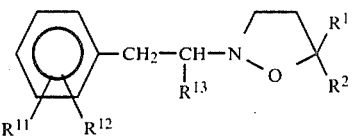
| Nr. | R[11] | R[12] | R[13] | R[2] | R[1] | 1 H—NMR CDCl/ppm |
|---|---|---|---|---|---|---|
| 205 | 2F | H | $CH_3$ | 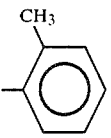 | H | 7,3–7,0 m; 5,3 t; 3,3–2,05 m; 3,36s, 3,16s, 1,1 d |
| 206 | 2-F | H | $CH_3$ |  | $CH_3$ | 7,4–7,0 m; 3,5–2,4 m; 1,55s, 1,05 d |
| 207 | 2-F | H | $CH_3$ | 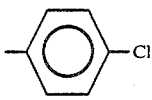 | H | 7,4–7,0 m; 5,02 t, 3,4–2,05 m; 1,15 d 1,09 d |
| 208 | 2-F | H | $CH_3$ | 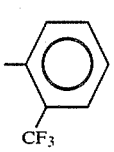 | H | 7,4–7,0 m; 5,44 t; 3,30–2,5 m; 1,12 d |
| 209 | 2-F | H | $CH_3$ | 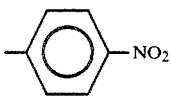 | H | 8,3–7,0 m; 5,16 t; 3,4–2,0 m; 1,10 d |
| 210 | 2-F | H | $CH_3$ | 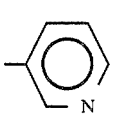 | H | |
| 211 | 2-Cl | 6-Cl | $CH_3$ | 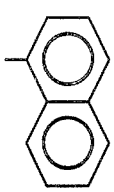 | H | |
| 212 | 2-Cl | 6-Cl | $CH_3$ | 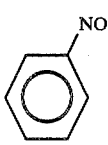 | H | |
| 213 | 3-Cl | 4-Cl | H | 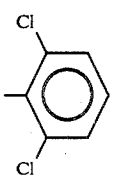 | H | |

-continued
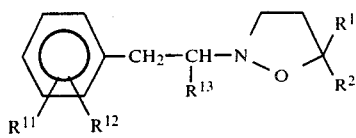
| Nr. | R[11] | R[12] | R[13] | R[2] | R[1] | 1 H—NMR CDCl/ppm |
|---|---|---|---|---|---|---|
| 214 | 3-Cl | 4-Cl | H | naphthyl | H | |
| 215 | 3-Cl | 4-Cl | CH$_3$ | naphthyl | H | |
| 216 | 2-Cl | 6-Cl | H | 2,6-dichlorophenyl | H | |
| 217 | 2-F | H | —C$_2$H$_5$ | naphthyl | H | |
| 218 | 2-F | H | —C$_2$H$_5$ | 2,6-dimethylphenyl | H | |
| 219 | 2-F | H | —C$_2$H$_5$ | naphthyl | H | |
| 220 | 2-F | H | —C$_2$H$_5$ | 2,6-dimethylphenyl | H | |

-continued
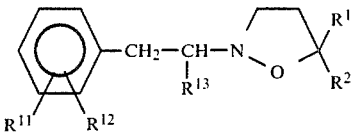
| Nr. | R¹¹ | R¹² | R¹³ | R² | R¹ | 1 H—NMR CDCl/ppm |
|---|---|---|---|---|---|---|
| 221 | 3-Cl | H | CH₃ | 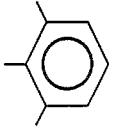 | H | |
| 222 | 2-Cl | H | —C₂H₅ | 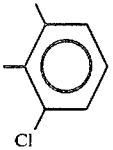 | H | |
| 223 | 2-Cl | H | —C₂H₅ | 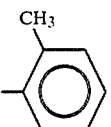 | H | |
| 224 | 2-Cl | H | —C₂H₅ | 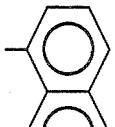 | H | |
| 225 | 2-F | H | CH₃ | 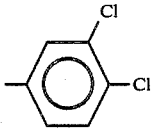 | H | 8,0–7,0 m; 5,8 m; 3,5–2,3 m; 1,1 d |
| 226 | 2-F | H | CH₃ | 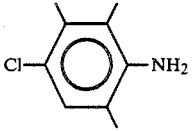 | H | 7,5–7,0 m; 5,0 t; 3,3–2,7 m; 2,1 t; 1,1 d |
| 227 | 2-F | H | CH₃ | 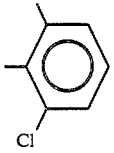 | H | 7,1–6,8 m; 5,6 t; 4,5s; 3,4–2,9 m; 2,5 m; 1,0 d |
| 228 | 4-Cl | H | CH₃ | | H | 7,3–7,0 m; 5,8–5,7 m; 3,4–3,0 m; 2,7–2,5 m; 1,0 d |

-continued
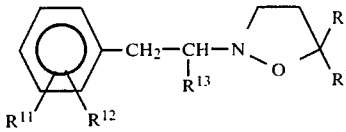
| Nr. | R¹¹ | R¹² | R¹³ | R² | R¹ | 1 H—NMR CDCl/ppm |
|---|---|---|---|---|---|---|
| 229 | 4-OCH₃ | H | CH₃ | 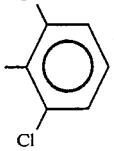 | H | 7,3–6,8 m; 5,8 t; 3,7s; 3,4–3,0 m; 2,7–2,4 m; 1,0 d |
| 230 | 2-F | H | CH₃ | 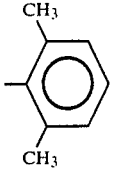 | H | 7,3–6,9 m; 5,4 t; 3,5–3,0 m; 2,5s; 1,0 d |
| 231 | 2-Br | H | CH₃ | 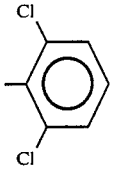 | H | 7,5–7,0 m; 5,9–5,6 m; 3,6–3,2 m; 2,8—2,5 m; 1,1 d |
| 232 | 2-CH₃ | H | CH₃ | 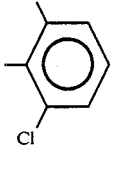 | H | 7,3–7,0 m; 5,8 t; 3,5–3,1 m; 2,7–2,5 m; 2,4s; 1,1 d |
| 233 | 2-F | H | CH₃ |  | H | 8,6 d; 7,4–7,0 m; 5,1 m; 3,4–2,6 m; 1,1 d |
| 234 | 2-F | H | CH₃ |  | H | 8,6 m; 7,7–7,0 m; 5,2 m; 3,4–2,6 m; 1,1 d |
| 235 | 2-F | H | CH₃ |  | H | 7,2–6,8 m; 3,6 m; 3,3–1,2 m; 1,0 d |
| 236 | 2-F | H | CH₃ | 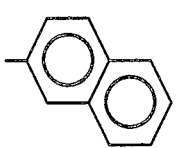 | H | 7,8–7,0 m; 5,3 m; 3,3–2,6 m; 1,1 d |
| 237 | 2-F | H | CH₃ | 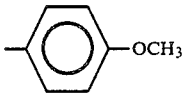 | H | 7,4–6,9 m; 5,0 m; 3,8s; 3,3–2,6 m; 1,1 d |

-continued

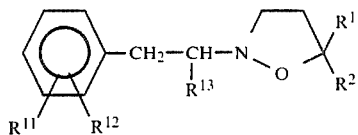

| Nr. | R11 | R12 | R13 | R2 | R1 | 1 H—NMR CDCl/ppm |
|-----|-----|-----|-----|-----|-----|------------------|
| 238 | H | H | H | Cl–[benzene]–Cl | H | 7,3–7,1 m; 5,8 m; 3,5–2,5 m |
| 239 | H | H | CH3 | Cl–[benzene]–Cl | H | 7,3–7,1 m; 5,8 t; 3,4–2,5 m; 1,1 d |
| 240 | H | H | CH3 | [naphthyl] | H | 8,0–7,2 m; 5,8 m; 3,4–2,6 m; 1,1 d |
| 241 | H | H | CH3 | [cyclohexyl-H] | H | 7,3–7,1 m; 3,8–3,6 m; 3,4–1,2 m; 1,1 d |
| 242 | 2-CH3 | H | CH3 | CH3–[benzene]–CH3 | H | 7,2–7,0 m; 5,5 t; 3,4–2,6 m; 2,4s; 1,1 d |
| 243 | 2-CH3 | H | CH3 | [naphthyl] | H | 8,0–7,1 m; 5,8 m; 3,3–2,6 m; 2,4s; 1,1 d |
| 244 | 2-CH3 | H | CH3 | [cyclohexyl-H] | H | 7,1 m; 3,8 m; 3,3–1,5 m; 2,4s; 1,0 d |

Preparation of the new hydroxylamines of the formula V.

EXAMPLE a 1,001 g (10 mol) of pinacolone and 822 g (11.8 mol) of hydroxylamine HCl are heated at the reflux temperature with 985 g (12 mol) of sodium acetate in 5 l of ethanol for 12 hours. After the mixture hs been filtered and the filtrate has been concentrated on a rotary evaporator, the residue is extracted by shaking with ether. 954 g of pinacolone oxime of melting point 69° C. (82% yield) are obtained from the ether phase.

115.16 g (1 mol) of pinacolone oxime are dissolved in 500 ml of methanol and the solution is brought to pH 3 with concentrated HCl, against bromocresol green indicator. 62.8 g (1 mol) of NaBH3CN are added in small portions, while cooling the batch with ice. During this addition, the pH value is kept at 3 by dropwise addition of concentrated HCl. When the addition has ended, stirring is continued at room temperature for 3 hours.

The batch is brought to pH 1 by careful dropwise addition of concentrated HCl, in order to decompose residual borohydride. The mixture is concentrated on a Rotavapor (together with the precipitate), and the residue is extracted three times with 500 ml of chloroform each time. After drying over Na$_2$SO$_4$, the chloroform is concentrated. The residue crystallises out.

Yield: 124 g (81%), melting point: 115° C. (HCl salt), 51° C. (base).

The following compounds are obtained analogously

| | Compound | Example | Yield | physical data $^1$H—NMR 60 MHZ CDCl$_3$ |
|---|---|---|---|---|
| a | (CH$_3$)$_2$C(CH$_3$)—NHOH | × HCl | 81% | m.p. 115° C. [HCl] 51° C. base |
| b | (CH$_3$)$_2$CH—CH$_2$—NHOH | × HCL | 85% | 3.16 [2 × α] 1.10 [2 × α] |
| c | (CH$_3$)$_2$CH—CH(CH$_3$)—NHOH | × HCl | 80% | 1.36 [α] 1.01 [2 × α] |
| d | cyclopropyl-C(CH$_3$)—NHOH | × HCl | 80% | 1.40 [α] 0.66 [mult] |
| e | (CH$_3$)$_3$C—C(NHOH)—CH$_2$—F | × HCL | 85% | 4.66 [s] 3.93 [s] |
| f | dicyclopropyl-CH—NHOH | × HCl | 60% | 1.18 [α] 1.10 [α] m.p. 75° C. |
| J | 1-methylcyclopropyl-C(CH$_3$)—NHOH | × HCl | 40% | 1.43 [ ] 1.13 [ ] |
| h | (CH$_3$)$_3$C—CH$_2$—NHOH | × HCl | 80% | 3.13 [s] 1.10 [s] |
| i | naphthyl-CH$_2$—NHOH | × HCl | 76% | m.p.: 205° C. |
| k | (2-F-C$_6$H$_4$)—CH$_2$—CH(CH$_3$)—NHOH | × HCl | 25% | m.p.: 82° C. |
| l | CH$_2$=CH—CH$_2$—C(CH$_3$)$_2$—C(CH$_3$)$_2$—NHOH | × HCl | 59% | 4.8–5.6 [m] 1.4 [α] 1.13 [s] 1.00 [s] |

-continued

| Compound | Example | Yield | physical data $^1$H—NMR 60 MHZ CDCl$_3$ |
|---|---|---|---|
| m  HO—CH$_2$—C(CH$_3$)(CH$_3$)—C(CH$_3$)—NHOH  × HCl | | 62% | 3.3–3.8 [m]<br>1.40 [ ]<br>0.93 [s]<br>0.80 [s] |
| n  (CH$_3$)$_2$C=CH—CH$_2$—CH$_2$—C(CH$_3$)—NHOH  × HCl | | 98% | 3.5 [m]<br>1.01–1.8 [m] |
| o  (menthyl-type structure with =C(CH$_3$)$_2$ and NHOH, CH$_3$)  HCl | | 90% | 0.8–2.00 [m] |
| p  biphenyl-O—C(CH$_3$)$_2$—CH(CH$_3$)—NHOH  HCl | | 71% | 124° C. |
| q  2,4-dichlorophenyl-O—CH$_2$—C(CH$_3$)—NHOH with C(CH$_3$)$_3$  × HCl | | 86% | 139° C. |
| 4-Cl-C$_6$H$_4$—CH$_2$—CH(CH$_3$)—NHOH  × HCl | | 75% | m.p. 135° C. |
| 4-Cl-C$_6$H$_4$—CH(cyclopropyl)—NHOH  × HCl | | 78% | 7.33 (m)<br>3.67 (bt)<br>6.70 (m) |
| 4-F-C$_6$H$_4$—CH$_2$—CH(CH$_3$)—NHOH  × HCl | | 85% | 6.96 (d)<br>6.76 (d)<br>1.30 (d) |

EXAMPLE a$_1$

Preparation of the new alkenes of the formula VII 4-Amino-3,5-dichloro-styrene 4.75 g (0.025 mol) of 4-amino-3,5-dichloro-benzaldehyde are heated at the reflux temperature in 50 ml of dioxane with 13.4 g (0.0375 mol) of methyl-triphenylphosphonium bromide and 5.2 g of potassium carbonate, with the addition of 0.75 ml of water, for 3 hours.

After cooling, the precipitate is filtered off with suction, the filtrate is concentrated in vacuo and the residue is triturated with a large quantity of cyclohexane. The cyclohexane phase is concentrated and the residue is chromatographed over silica gel on a short column. 4.5 g (95%) of 4-amino-3,5-dichlorostyrene of melting point 63° C. are obtained.

We claim:

1. A method of combating insects, arachnids, nematodes or fungi which comprises applying to such insects, arachnids, nematodes or fungi or to a habitat thereof an insecticidally, arachnicidally, nematicidally or fungicidally effective amount of a substituted isoxazolidine of the formula

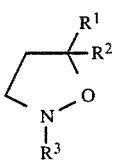

in which $R^1$ represents $C_{1-5}$-alkyl, $C_{3-6}$-cycloalkyl, phenyl-$C_{1-4}$-alkyl, phenyl, naphthyl or pyridyl, which can be substituted by nitro, OH, CN, halogen, $C_{1-4}$-alkyl, $C_{3-6}$-cycloalkyl, $C_{1-4}$-alkoxy, $C_{1-4}$-alkylthio, $C_{1-4}$-halogenoalkyl, $C_{1-4}$-alkoxycarbonyl, carboxyl (COOH), amino, $C_{1-4}$-alkylamino, di-$C_{1-4}$-alkylamino, phenylamino, phenyl-$C_{1-4}$-alkylamino, aminocarbonyl-$C_{1-4}$-alkyl, (—NHCOC$_{1-4}$-alkyl), $C_{1-4}$-alkylsulphonylamino (—NHSO$_2$C$_{1-4}$-alkyl), $C_{1-4}$-halogenoalkoxy, $C_{1-4}$-halogenoalkylthio, $C_{1-4}$-alkylenedioxy, $C_{1-4}$-halogenoalkylenedioxy, phenyl, naphthyl, phenoxy or naphthoxy, or represents a radical of the formula —COR$^4$, $R^4$ represents $C_{1-4}$-alkyl, phenyl, $C_{1-4}$-alkylthio, phenoxy, phenylthio, amino, $C_{1-4}$-alkylamino, di-$C_{1-4}$-alkylamino, phenylamino, naphthylamino, phenyl-$C_{1-4}$-alkylamino, diphenylamino, $C_{3-6}$-cycloalkylamino, morpholino or piperidino, $R^2$ represents hydrogen or one of the radicals mentioned under $R^1$, and $R^3$ represents $C_{1-10}$-alkyl, $C_{3-6}$-cycloalkyl, $C_{2-4}$-alkenyl, $C_{2-6}$-alkinyl, phenyl or naphthyl, or represents $C_{1-6}$-alkyl, which is substituted by halogen, OH, CN, amino, $C_{1-4}$-alkylamino, $C_{1-4}$-di-alkylamino, $C_{1-4}$-alkoxy, $C_{3-6}$-cycloalkyl, phenyl, naphthyl, phenoxy, phenylthio or $C_{1-4}$-alkylcarbonyloxy; or represents phenyl which is substituted by halogen, NO$_2$, CN, OH, amino, $C_{1-4}$-alkylamino, di-$C_{1-4}$-alkylamino, or (—COOC$_{1-4}$-alkyl), or represents phenoxy, naphthyloxy or biphenyloxy, or an acid addition salt thereof.

2. The method according to claim 1, in which
$R^1$ represents phenyl or phenyl substituted by halogen, $C_{1-4}$-alkyl, methoxy, nitro, trifluoromethyl, trifluoromethoxy, CN, —COOCH$_3$, COOH, amino, —NHCOCH$_3$, methylenedioxy, phenoxy, or halogen-substituted phenoxy; $C_{1-5}$-alkyl, or $C_{1-5}$-alkyl which is substituted by halogen, cyclopropyl, cyclohexyl, hydroxyl, $C_{1-4}$-alkoxy, phenyl or phenyl substituted by halogen or methoxy; or pyridyl, or pyridyl which is substituted by methyl or halogen; or —COR$^4$, $R^2$ represents hydrogen, phenyl $C_{1-4}$-alkyl, chlorophenyl or —COR$^4$, $R^4$ represents $C_{1-4}$-alkoxy, or di-$C_{1-4}$-alkylamino, and $R^3$ represents $C_{1-6}$-alkyl unsubstituted or substituted by cyclopropyl, halogen, OH or phenyl, or represents naphthyl, phenyl, halogenophenoxy, naphthyloxy or biphenyloxy.

3. The method according to claim 1, in which $R^3$ represents $C_{1-6}$-alkyl or $C_{1-6}$-alkyl substituted by halogen, cyclopropyl, cyclohexyl, hydroxyl, $C_{1-4}$-alkoxy, phenyl or phenyl substituted by halogen or methoxy.

4. The method according to claim 1, in which $R^1$ represents phenyl or naphthyl unsubstituted or substituted by nitro, OH, CN, halogen, $C_{1-4}$-alkyl, $C_{3-6}$-cycloalkyl, $C_{1-4}$-alkoxy, $C_{1-4}$-alkylthio, $C_{1-4}$-halogenoalkyl, $C_{1-4}$-alkoxycarbonyl, carboxyl (COOH), amino, $C_{1-4}$-alkylamino, di-$C_{1-4}$-alkylamino, arylamino, phenyl-$C_{1-4}$-alkylamino, aminocarbonyl-$C_{1-4}$-alkyl, (—NHCOC$_{1-4}$-alkyl), $C_{1-4}$-alkylsulphonylamino (—NHSO$_2$C$_{1-4}$-alkyl), $C_{1-4}$-halogenoalkoxy, $C_{1-4}$-halogenoalkylthio, $C_{1-4}$-alkylenedioxy, $C_{1-4}$-halogenoalkylenedioxy, phenyl, naphthyl, phenoxy or naphthoxy, and $R^2$ represents hydrogen.

5. A method of fattening an animal which comprises supplying to said animal along with its feed an amount effective to increase the utilization of the feed of a substituted or isoxazolidine of the formula

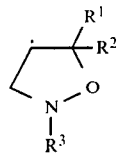

in which
$R^1$ represents $C_{1-5}$-alkyl, $C_{3-6}$-cycloalkyl, phenyl-$C_{1-4}$-alkyl, phenyl, naphthyl or pyridyl, which can be substituted by nitro, OH, CN, halogen, $C_{1-4}$-alkyl, $C_{3-6}$-cycloalkyl, $C_{1-4}$-alkoxy, $C_{1-4}$-alkylthio, $C_{1-4}$-halogenoalkyl, $C_{1-4}$-alkoxycarbonyl, carboxyl, (COOH), amino, $C_{1-4}$-alkylamino di-$C_{1-4}$-alkylamino, phenylamino, phenyl-$C_{1-4}$-alkylamino, aminocarbonyl-$C_{1-4}$-alkyl, (—NHCOC$_{1-4}$-alkyl), $C_{1-4}$-alkylsulphonylamino (—NHSO$_2$C$_{1-4}$-alkyl), $C_{1-4}$-halogenoalkoxy, $C_{1-4}$-halogenoalkylthio, $C_{1-4}$-alkylenedioxy, $C_{1-4}$-halogenoalkylenedioxy, phenyl, naphthyl, phenoxy or naphthoxy, or represents a radical of the formula —COR$^4$, $R^4$ represents $C_{1-4}$-alkyl, phenyl, $C_{1-4}$-alkylthio, phenoxy, phenylthio, amino, $C_{1-4}$-alkylamino, di-$C_{1-4}$-alkylamino, phenylamino, naphthylamino, phenyl-$C_{1-4}$-alkylamino, diphenylamino, $C_{3-6}$-cycloalkylamino, morpholino or piperidino, $R^2$ represents hydrogen or one of the radicals mentioned under $R^1$, and $R^3$ represents $C_{1-10}$-alkyl, $C_{3-6}$-cycloalkyl, $C_{2-4}$-alkenyl, $C_{2-6}$-alkinyl, phenyl or naphthyl, or represents $C_{1-6}$-alkyl, which is substituted by halogen, OH, CN, amino, $C_{1-4}$-alkylamino, $C_{1-4}$-di-alkylamino, $C_{1-4}$-alkoxy, $C_{3-6}$-cycloalkyl, phenyl, naphthyl, phenoxy, phenylthio or $C_{1-4}$-alkylcarbonyloxy; or represents phenyl which is substituted by halogen, NO$_2$, CN, OH, amino, $C_{1-4}$-alkylamino, di-$C_{1-4}$-alkylamino, or (—COOC$_{1-4}$-alkyl), or represents phenoxy, naphthyloxy or biphenyloxy, or an acid addition salt thereof.

6. A method according to claim 5, in which
$R^1$ represents phenyl or phenyl substituted by halogen, $C_{1-4}$-alkyl, methoxy, nitro, trifluoromethyl, trifluoromethoxy, CN, —COOCH$_3$, COOH, amino, —NHCOCH$_3$, methylenedioxy, phenoxy, or halogen-substituted phenoxy; $C_{1-5}$-alkyl, or $C_{1-5}$-alkyl which is substituted by halogen, cyclopropyl, cyclohexyl, hydroxyl, $C_{1-4}$-alkoxy, phenyl or phenyl substituted by halogen or methoxy; or pyridyl, or pyridyl which is substituted by methyl or halogen; or —COR$^4$, $R^2$ represents hydrogen, phenyl $C_{1-4}$-alkyl, chlorophenyl or —COR$^4$, $R^4$ represents $C_{1-4}$-alkoxy, or di-$C_{1-4}$-alkylamino, and $R^3$ represents $C_{1-6}$-alkyl unsubstituted or substituted by cyclopropyl, halogen, OH or phenyl, or represents naphthyl, phenyl, halogenophenoxy, naphthyloxy or biphenyloxy.

7. A method according to claim 5, in which $R^3$ represents $C_{1-6}$-alkyl or $C_{1-6}$-alkyl substituted by halogen, cyclopropyl, cyclohexyl, hydroxyl, $C_{1-4}$-alkoxy, phenyl or phenyl substituted by halogen or methoxy.

8. A method according to claim 5, in which
$R^1$ represents phenyl or naphthyl unsubstituted or substituted by nitro, OH, CN, halogen, $C_{1-4}$-alkyl, $C_{3-6}$-cycloalkyl, $C_{1-4}$-alkoxy, $C_{1-4}$-alkylthio, $C_{1-4}$-halogenoalkyl, $C_{1-4}$-alkoxycarbonyl, carboxyl (COOH), amino, $C_{1-4}$-alkylamino, di-$C_{1-4}$-alkylamino, arylamino, phenyl-$C_{1-4}$-alkylamino, aminocarbonyl-$C_{1-4}$-alkyl, (—NHCO$C_{1-4}$-alkyl), $C_{1-4}$-alkylsulphonylamino (—NHSO$_2C_{1-4}$-alkyl), $C_{1-4}$-halogenoalkoxy, $C_{1-4}$-halogenoalkylthio, $C_{1-4}$-alkylenedioxy, $C_{1-4}$-halogenoalkylenedioxy, phenyl, naphthyl, phenoxy or naphthoxy, and $R^2$ represents hydrogen.

* * * * *